United States Patent
Jansen et al.

(10) Patent No.: US 6,979,532 B2
(45) Date of Patent: Dec. 27, 2005

(54) PROCESS FOR IDENTIFYING SUBSTANCES WHICH MODULATE THE ACTIVITY OF HYPERPOLARIZATION-ACTIVATED CATION CHANNELS

(75) Inventors: Hans-Willi Jansen, Niedernhausen (DE); Andrea Brüggemann, Frankfurt am Main (DE); Holger Heitsch, Mainz-Kastel (DE); Heinz Gögelein, Frankfurt am Main (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 139 days.

(21) Appl. No.: 10/067,457

(22) Filed: Feb. 7, 2002

(65) Prior Publication Data

US 2003/0082513 A1 May 1, 2003

Related U.S. Application Data

(63) Continuation of application No. 09/779,587, filed on Feb. 9, 2001, now abandoned.

(30) Foreign Application Priority Data

Feb. 12, 2000 (DE) .......................................... 100 06 309

(51) Int. Cl.⁷ .............................. C12Q 1/00; C12Q 1/08; C12N 5/02; C07K 14/00
(52) U.S. Cl. .............................. 435/4; 435/40; 435/404; 530/350
(58) Field of Search .............................. 435/4, 40, 404, 435/40.5; 530/350

(56) References Cited

U.S. PATENT DOCUMENTS 6,420,183 B1 * 7/2002 Krahn et al. ................. 436/164

FOREIGN PATENT DOCUMENTS

| WO | WO 99/11784 | 3/1999 |
|---|---|---|
| WO | WO 99/32615 | 7/1999 |
| WO | WO 99/42574 | 8/1999 |
| WO | WO 00/63349 | 10/2000 |
| WO | WO 00/73431 | 12/2000 |

OTHER PUBLICATIONS

Hodder, et al, 2004, J. Biomol. Screening, 9(5): 417–426.*

Vaccari, T. et al., "The Human Gene Coding for HCN2, a Pacemaker Channel of the Heart", Biochim. et Biophys. Acta 1446(3):419–425, 1999.

Biel, M. et al., "Hyperpolarization–Activated Cation Channels: A Multi–Gene Family", *Rev. Physiol. Biochem. Pharmacol.* 136:165–181, 1999.

Hamill, O.P. et al., "Improved Patch–Clamp Techniques for High–Resolution Current Recording from Cells and Cell–Free Membrane Patches", *Pflügers Arch.* 391:85–100, 1981.

Ludwig, A. et al., "Two Pacemaker Channels from Human Heart with Profoundly Different Activation Kinetics", *EMBO J.* 18(9):2323–2329, 1999.

Langheinrich, U. and Jürgen Daut, "Hyperpolarization of isolated capillaries from guinea–pig heart induced by K+ channel openers and glucose deprivation",*Journal of Physiolog*, 502.2:397–408, 1997.

* cited by examiner

*Primary Examiner*—Lorraine Spector
*Assistant Examiner*—Sandra Wegert

(57) ABSTRACT

The present invention provides a process for identifying substances that modulate the activity of hyperpolarization-activated cation channels, and the use of this process.

31 Claims, No Drawings

SEQUENCE LISTING

<160> NUMBER OF SEQ ID NOS: 10

<210> SEQ ID NO 1
<211> LENGTH: 889
<212> TYPE: PRT
<213> ORGANISM: Homo sapiens

<400> SEQUENCE: 1

```
Met Asp Ala Arg Gly Gly Gly Arg Pro Gly Glu Ser Pro Gly Ala
  1               5                  10                  15

Ser Pro Thr Thr Gly Pro Pro Pro Pro Pro Pro Arg Pro Pro Lys
                 20                  25                  30

Gln Gln Pro Pro Pro Pro Pro Pro Ala Pro Pro Pro Gly Pro Gly
                 35                  40                  45

Pro Ala Pro Pro Gln His Pro Pro Arg Ala Glu Ala Leu Pro Pro Glu
         50                  55                  60

Ala Ala Asp Glu Gly Gly Pro Arg Gly Arg Leu Arg Ser Arg Asp Ser
 65                  70                  75                  80
```

-continued

```
Ser Cys Gly Arg Pro Gly Thr Pro Gly Ala Ala Ser Thr Ala Lys Gly
                85                  90                  95

Ser Pro Asn Gly Glu Cys Gly Arg Gly Glu Pro Gln Cys Ser Pro Ala
            100                 105                 110

Gly Pro Glu Gly Pro Ala Arg Gly Pro Lys Val Ser Phe Ser Cys Arg
        115                 120                 125

Gly Ala Ala Ser Gly Pro Ala Pro Gly Pro Gly Pro Ala Glu Glu Ala
    130                 135                 140

Gly Ser Glu Glu Ala Gly Pro Ala Gly Glu Pro Arg Gly Ser Gln Ala
145                 150                 155                 160

Ser Phe Met Gln Arg Gln Phe Gly Ala Leu Leu Gln Pro Gly Val Asn
                165                 170                 175

Lys Phe Ser Leu Arg Met Phe Gly Ser Gln Lys Ala Val Glu Arg Glu
            180                 185                 190

Gln Glu Arg Val Lys Ser Ala Gly Ala Trp Ile Ile His Pro Tyr Ser
        195                 200                 205

Asp Phe Arg Phe Tyr Trp Asp Phe Thr Met Leu Leu Phe Met Val Gly
    210                 215                 220

Asn Leu Ile Ile Ile Pro Val Gly Ile Thr Phe Phe Lys Asp Glu Thr
225                 230                 235                 240

Thr Ala Pro Trp Ile Val Phe Asn Val Val Ser Asp Thr Phe Phe Leu
                245                 250                 255

Met Asp Leu Val Leu Asn Phe Arg Thr Gly Ile Val Ile Glu Asp Asn
            260                 265                 270

Thr Glu Ile Ile Leu Asp Pro Glu Lys Ile Lys Lys Tyr Leu Arg
        275                 280                 285

Thr Trp Phe Val Val Asp Phe Val Ser Ser Ile Pro Val Asp Tyr Ile
    290                 295                 300

Phe Leu Ile Val Glu Lys Gly Ile Asp Ser Glu Val Tyr Lys Thr Ala
305                 310                 315                 320

Arg Ala Leu Arg Ile Val Arg Phe Thr Lys Ile Leu Ser Leu Leu Arg
                325                 330                 335

Leu Leu Arg Leu Ser Arg Leu Ile Arg Tyr Ile His Gln Trp Glu Glu
            340                 345                 350

Ile Phe His Met Thr Tyr Asp Leu Ala Ser Ala Val Met Arg Ile Cys
        355                 360                 365

Asn Leu Ile Ser Met Met Leu Leu Leu Cys His Trp Asp Gly Cys Leu
    370                 375                 380

Gln Phe Leu Val Pro Met Leu Gln Asp Phe Pro Arg Asn Cys Trp Val
385                 390                 395                 400

Ser Ile Asn Gly Met Val Asn His Ser Trp Ser Glu Leu Tyr Ser Phe
                405                 410                 415

Ala Leu Phe Lys Ala Met Ser His Met Leu Cys Ile Gly Tyr Gly Arg
            420                 425                 430

Gln Ala Pro Glu Ser Met Thr Asp Ile Trp Leu Thr Met Leu Ser Met
        435                 440                 445

Ile Val Gly Ala Thr Cys Tyr Ala Met Phe Ile Gly His Ala Thr Ala
    450                 455                 460

Leu Ile Gln Ser Leu Asp Ser Ser Arg Arg Gln Tyr Gln Glu Lys Tyr
465                 470                 475                 480

Lys Gln Val Glu Gln Tyr Met Ser Phe His Lys Leu Pro Ala Asp Phe
                485                 490                 495
```

-continued

```
Arg Gln Lys Ile His Asp Tyr Tyr Glu His Arg Tyr Gln Gly Lys Met
            500                 505                 510

Phe Asp Glu Asp Ser Ile Leu Gly Glu Leu Asn Gly Pro Leu Arg Glu
            515                 520                 525

Glu Ile Val Asn Phe Asn Cys Arg Lys Leu Val Ala Ser Met Pro Leu
            530                 535                 540

Phe Ala Asn Ala Asp Pro Asn Phe Val Thr Ala Met Leu Thr Lys Leu
545                 550                 555                 560

Lys Phe Glu Val Phe Gln Pro Gly Asp Tyr Ile Ile Arg Glu Gly Thr
                565                 570                 575

Ile Gly Lys Lys Met Tyr Phe Ile Gln His Gly Val Val Ser Val Leu
            580                 585                 590

Thr Lys Gly Asn Lys Glu Met Lys Leu Ser Asp Gly Ser Tyr Phe Gly
            595                 600                 605

Glu Ile Cys Leu Leu Thr Arg Gly Arg Arg Thr Ala Ser Val Arg Ala
            610                 615                 620

Asp Thr Tyr Cys Arg Leu Tyr Ser Leu Ser Val Asp Asn Phe Asn Glu
625                 630                 635                 640

Val Leu Glu Glu Tyr Pro Met Met Arg Arg Ala Phe Glu Thr Val Ala
                645                 650                 655

Ile Asp Arg Leu Asp Arg Ile Gly Lys Lys Asn Ser Ile Leu Leu His
            660                 665                 670

Lys Val Gln His Asp Leu Asn Ser Gly Val Phe Asn Asn Gln Glu Asn
            675                 680                 685

Ala Ile Ile Gln Glu Ile Val Lys Tyr Asp Arg Glu Met Val Gln Gln
            690                 695                 700

Ala Glu Leu Gly Gln Arg Val Gly Leu Phe Pro Pro Pro Pro Pro Pro
705                 710                 715                 720

Pro Gln Val Thr Ser Ala Ile Ala Thr Leu Gln Gln Ala Ala Ala Met
                725                 730                 735

Ser Phe Cys Pro Gln Val Ala Arg Pro Leu Val Gly Pro Leu Ala Leu
            740                 745                 750

Gly Ser Pro Arg Leu Val Arg Arg Pro Pro Gly Pro Ala Pro Ala
            755                 760                 765

Ala Ala Ser Pro Gly Pro Pro Pro Ala Ser Pro Pro Gly Ala Pro
770                 775                 780

Ala Ser Pro Arg Ala Pro Arg Thr Ser Pro Tyr Gly Gly Leu Pro Ala
785                 790                 795                 800

Ala Pro Leu Ala Gly Pro Ala Leu Pro Ala Arg Arg Leu Ser Arg Ala
                805                 810                 815

Ser Arg Pro Leu Ser Ala Ser Gln Pro Ser Leu Pro His Gly Ala Pro
            820                 825                 830

Gly Pro Ala Ala Ser Thr Arg Pro Ala Ser Ser Ser Thr Pro Arg Leu
            835                 840                 845

Gly Pro Thr Pro Ala Ala Arg Ala Ala Ala Pro Ser Pro Asp Arg Arg
            850                 855                 860

Asp Ser Ala Ser Pro Gly Ala Ala Gly Gly Leu Asp Pro Gln Asp Ser
865                 870                 875                 880

Ala Arg Ser Arg Leu Ser Ser Asn Leu
                885
```

<210> SEQ ID NO 2
<211> LENGTH: 3372
<212> TYPE: DNA

<213> ORGANISM: Homo sapiens

<400> SEQUENCE: 2

| | | | | | |
|---|---|---|---|---|---|
| cggctccgct | ccgcactgcc | cggcgccgcc | tcgccatgga | cgcgcgcggg | ggcggcgggc | 60 |
| ggcccgggga | gagcccgggc | gcgagcccca | cgaccgggcc | gccgccgccg | ccgccccgc | 120 |
| gccccccaa | acagcagccg | ccgccgccg | cgccgcccgc | gccccccg | ggccccgggc | 180 |
| ccgcgccccc | ccagcacccg | ccccgggccg | aggcgttgcc | cccggaggcg | gcggatgagg | 240 |
| gcggcccgcg | gggccggctc | cgcagccgcg | acagctcgtg | cggccgcccc | ggcaccccgg | 300 |
| gcgcggcgag | cacggccaag | ggcagcccga | acggcgagtg | cgggcgcggc | gagccgcagt | 360 |
| gcagccccgc | ggggcccgag | ggccggcgc | gggggcccaa | ggtgtcgttc | tcgtgccgcg | 420 |
| gggcggcctc | ggggcccgcg | ccggggccgg | ggccggcgga | ggaggcgggc | agcgaggagg | 480 |
| cgggcccggc | gggggagccg | cgcggcagcc | aggccagctt | catgcagcgc | cagttcggcg | 540 |
| cgctcctgca | gccgggcgtc | aacaagttct | cgctgcggat | gttcggcagc | cagaaggccg | 600 |
| tggagcgcga | gcaggagcgc | gtcaagtcgg | cgggggcctg | gatcatccac | ccgtacagcg | 660 |
| acttcaggtt | ctactgggac | ttcaccatgc | tgctgttcat | ggtgggaaac | ctcatcatca | 720 |
| tcccagtggg | catcaccttc | ttcaaggatg | agaccactgc | cccgtggatc | gtgttcaacg | 780 |
| tggtctcgga | caccttcttc | ctcatggacc | tggtgttgaa | cttccgcacc | ggcattgtga | 840 |
| tcgaggacaa | cacggagatc | atcctggacc | ccgagaagat | caagaagaag | tatctgcgca | 900 |
| cgtggttcgt | ggtggacttc | gtgtcctcca | tccccgtgga | ctacatcttc | cttatcgtgg | 960 |
| agaagggcat | tgactccgag | gtctacaaga | cggcacgcgc | cctgcgcatc | gtgcgcttca | 1020 |
| ccaagatcct | cagcctcctg | cggctgctgc | gcctctcacg | cctgatccgc | tacatccatc | 1080 |
| agtgggagga | gatcttccac | atgacctatg | acctggccag | cgcggtgatg | aggatctgca | 1140 |
| atctcatcag | catgatgctg | ctgctctgcc | actgggacgg | ctgcctgcag | ttcctggtgc | 1200 |
| ctatgctgca | ggacttcccg | cgcaactgct | gggtgtccat | caatggcatg | gtgaaccact | 1260 |
| cgtggagtga | actgtactcc | ttcgcactct | tcaaggccat | gagccacatg | ctgtgcatcg | 1320 |
| ggtacggccg | gcaggcgccc | gagagcatga | cggacatctg | gctgaccatg | ctcagcatga | 1380 |
| ttgtgggtgc | cacctgctac | gccatgttca | tcggccacgc | cactgccctc | atccagtcgc | 1440 |
| tggactcctc | gcggcgccag | taccaggaga | agtacaagca | ggtggagcag | tacatgtcct | 1500 |
| tccacaagct | gccagctgac | ttccgccaga | agatccacga | ctactatgag | caccgttacc | 1560 |
| agggcaagat | gtttgacgag | gacagcatcc | tgggcgagct | caacgggccc | ctgcgggagg | 1620 |
| agatcgtcaa | cttcaactgc | cggaagctgg | tggcctccat | gccgctgttc | gccaacgccg | 1680 |
| accccaactt | cgtcacggcc | atgctgacca | agctcaagtt | cgaggtcttc | cagccgggtg | 1740 |
| actacatcat | ccgcgaaggc | accatcggga | agaagatgta | cttcatccag | cacgcgtgg | 1800 |
| tcagcgtgct | cactaagggc | aacaaggaga | tgaagctgtc | cgatggctcc | tacttcgggg | 1860 |
| agatctgcct | gctcacccgg | ggccgccgca | cggcgagcgt | gcgggctgac | acctactgcc | 1920 |
| gcctctattc | gctgagcgtg | gacaacttca | acgaggtgct | ggaggagtac | ccatgatgc | 1980 |
| ggcgcgcctt | cgagacggtg | gccatcgacc | gcctggaccg | catcggcaag | aagaattcca | 2040 |
| tcctcctgca | caaggtgcag | catgacctca | actcgggcgt | attcaacaac | caggagaacg | 2100 |
| ccatcatcca | ggagatcgtc | aagtacgacc | gcgagatggt | gcagcaggcc | gagctgggtc | 2160 |
| agcgcgtggg | cctcttcccg | ccgccgccgc | cgccgccgca | ggtcacctcg | gccatcgcca | 2220 |
| cgctgcagca | ggcggcggcc | atgagcttct | gcccgcaggt | ggcgcggccg | ctcgtggggc | 2280 |

-continued

```
cgctggcgct cggctcgccg cgcctcgtgc gccgcccgcc cccggggccc gcacctgccg    2340
ccgcctcacc cgggcccccg ccccccgcca gcccccgggc gcgcccgcc agccccggg     2400 caccgcggac ctcgccctac ggcggcctgc ccgccgcccc ccttgctggg cccgccctgc    2460
ccgcgcgccg cctgagccgc gcgtcgcgcc cactgtccgc ctcgcagccc tcgctgcctc    2520
acggcgcccc cggcccgcg gcctccacac gcccggccag cagctccaca ccgcgcttgg     2580
ggcccacgcc cgctgcccgg gccgccgcgc ccagcccgga ccgcagggac tcggcctcac    2640
ccggcgccgc cggcggcctg gaccccagg actccgcgcg ctcgcgcctc tcgtccaact     2700
tgtgaccctc gccgaccgcc ccgcgggccc aggcgggccg ggggcgggc cgtcatccag     2760 accaaagcca tgccattgcg ctgccccggc cgccagtccg cccagaagcc atagacgaga    2820
cgtaggtagc cgtagttgga cggacgggca gggccggcgg ggcagccccc tccgcgcccc    2880
cggccgtccc ccctcatcgc cccgcgccca ccccatcgc ccctgccccc ggcggcggcc     2940
tcgcgtgcga gggggctccc ttcacctcgg tgcctcagtt cccccagctg taagacaggg    3000
acggggcggc ccagtggctg agaggagccg gctgtggagc cccgcccgcc cccacccctc    3060
taggtggccc ccgtccgagg aggatcgttt tctaagtgca atacttggcc cgccggcttc    3120
ccgctgcccc catcgcgctc acgcaataac cggcccggcc ccgtccgcg cgtccccc      3180 ggtgacctcg gggagcagca ccccgcctcc ctccagcact ggcaccgaga ggcaggcctg    3240
gctgcgcagg gcgcgggggg gaggctgggg tcccgccgcc gtgatgaatg tactgacgag    3300
ccgaggcagc agtgccccca ccgtggcccc ccacgcccca ttaaccccca cacccccatt    3360
ccgcgcaata aa                                                        3372
```

<210> SEQ ID NO 3
<211> LENGTH: 1203
<212> TYPE: PRT
<213> ORGANISM: Homo sapiens

<400> SEQUENCE: 3

```
Met Asp Lys Leu Pro Pro Ser Met Arg Lys Arg Leu Tyr Ser Leu Pro
  1               5                  10                  15

Gln Gln Val Gly Ala Lys Ala Trp Ile Met Asp Glu Glu Glu Asp Ala
             20                  25                  30

Glu Glu Glu Gly Ala Gly Gly Arg Gln Asp Pro Ser Arg Arg Ser Ile
         35                  40                  45

Arg Leu Arg Pro Leu Pro Ser Pro Ser Pro Ser Ala Ala Ala Gly Gly
     50                  55                  60

Thr Glu Ser Arg Ser Ser Ala Leu Gly Ala Ala Asp Ser Glu Gly Pro
 65                  70                  75                  80

Ala Arg Gly Ala Gly Lys Ser Thr Asn Gly Asp Cys Arg Arg Phe
             85                  90                  95

Arg Gly Ser Leu Ala Ser Leu Gly Ser Arg Gly Gly Ser Gly Gly
            100                 105                 110

Thr Gly Ser Gly Ser Ser His Gly His Leu His Asp Ser Ala Glu Glu
        115                 120                 125

Arg Arg Leu Ile Ala Glu Gly Asp Ala Ser Pro Gly Glu Asp Arg Thr
    130                 135                 140

Pro Pro Gly Leu Ala Ala Glu Pro Glu Arg Pro Gly Ala Ser Ala Gln
145                 150                 155                 160

Pro Ala Ala Ser Pro Pro Pro Gln Gln Pro Gln Pro Ala Ser
                165                 170                 175
```

-continued

```
Ala Ser Cys Glu Gln Pro Ser Val Asp Thr Ala Ile Lys Val Glu Gly
            180                 185                 190

Gly Ala Ala Gly Asp Gln Ile Leu Pro Glu Ala Glu Val Arg Leu
        195                 200                 205

Gly Gln Ala Gly Phe Met Gln Arg Gln Phe Gly Ala Met Leu Gln Pro
    210                 215                 220

Gly Val Asn Lys Phe Ser Leu Arg Met Phe Gly Ser Gln Lys Ala Val
225                 230                 235                 240

Glu Arg Glu Gln Glu Arg Val Lys Ser Ala Gly Phe Trp Ile Ile His
                245                 250                 255

Pro Tyr Ser Asp Phe Arg Phe Tyr Trp Asp Leu Thr Met Leu Leu Leu
            260                 265                 270

Met Val Gly Asn Leu Ile Ile Ile Pro Val Gly Ile Thr Phe Phe Lys
        275                 280                 285

Asp Glu Asn Thr Thr Pro Trp Ile Val Phe Asn Val Val Ser Asp Thr
    290                 295                 300

Phe Phe Leu Ile Asp Leu Val Leu Asn Phe Arg Thr Gly Ile Val Val
305                 310                 315                 320

Glu Asp Asn Thr Glu Ile Ile Leu Asp Pro Gln Arg Ile Lys Met Lys
                325                 330                 335

Tyr Leu Lys Ser Trp Phe Met Val Asp Phe Ile Ser Ser Ile Pro Val
            340                 345                 350

Asp Tyr Ile Phe Leu Ile Val Glu Thr Arg Ile Asp Ser Glu Val Tyr
        355                 360                 365

Lys Thr Ala Arg Ala Leu Arg Ile Val Arg Phe Thr Lys Ile Leu Ser
    370                 375                 380

Leu Leu Arg Leu Leu Arg Leu Ser Arg Leu Ile Arg Tyr Ile His Gln
385                 390                 395                 400

Trp Glu Glu Ile Phe His Met Thr Tyr Asp Leu Ala Ser Ala Val Val
                405                 410                 415

Arg Ile Val Asn Leu Ile Gly Met Met Leu Leu Leu Cys His Trp Asp
            420                 425                 430

Gly Cys Leu Gln Phe Leu Val Pro Met Leu Gln Asp Phe Pro Asp Asp
        435                 440                 445

Cys Trp Val Ser Ile Asn Asn Met Val Asn Asn Ser Trp Gly Lys Gln
    450                 455                 460

Tyr Ser Tyr Ala Leu Phe Lys Ala Met Ser His Met Leu Cys Ile Gly
465                 470                 475                 480

Tyr Gly Arg Gln Ala Pro Val Gly Met Ser Asp Val Trp Leu Thr Met
                485                 490                 495

Leu Ser Met Ile Val Gly Ala Thr Cys Tyr Ala Met Phe Ile Gly His
            500                 505                 510

Ala Thr Ala Leu Ile Gln Ser Leu Asp Ser Ser Arg Arg Gln Tyr Gln
        515                 520                 525

Glu Lys Tyr Lys Gln Val Glu Gln Tyr Met Ser Phe His Lys Leu Pro
    530                 535                 540

Pro Asp Thr Arg Gln Arg Ile His Asp Tyr Tyr Glu His Arg Tyr Gln
545                 550                 555                 560

Gly Lys Met Phe Asp Glu Glu Ser Ile Leu Gly Glu Leu Ser Glu Pro
                565                 570                 575

Leu Arg Glu Glu Ile Ile Asn Phe Asn Cys Arg Lys Leu Val Ala Ser
            580                 585                 590
```

```
Met Pro Leu Phe Ala Asn Ala Asp Pro Asn Phe Val Thr Ser Met Leu
        595                 600                 605

Thr Lys Leu Arg Phe Glu Val Phe Gln Pro Gly Asp Tyr Ile Ile Arg
        610                 615                 620

Glu Gly Thr Ile Gly Lys Lys Met Tyr Phe Ile Gln His Gly Val Val
625                 630                 635                 640

Ser Val Leu Thr Lys Gly Asn Lys Glu Thr Lys Leu Ala Asp Gly Ser
                645                 650                 655

Tyr Phe Gly Glu Ile Cys Leu Leu Thr Arg Gly Arg Arg Thr Ala Ser
                660                 665                 670

Val Arg Ala Asp Thr Tyr Cys Arg Leu Tyr Ser Leu Ser Val Asp Asn
        675                 680                 685

Phe Asn Glu Val Leu Glu Glu Tyr Pro Met Met Arg Arg Ala Phe Glu
        690                 695                 700

Thr Val Ala Leu Asp Arg Leu Asp Arg Ile Gly Lys Lys Asn Ser Ile
705                 710                 715                 720

Leu Leu His Lys Val Gln His Asp Leu Asn Ser Gly Val Phe Asn Tyr
                725                 730                 735

Gln Glu Asn Glu Ile Ile Gln Gln Ile Val Gln His Asp Arg Glu Met
                740                 745                 750

Ala His Cys Ala His Arg Val Gln Ala Ala Ser Ala Thr Pro Thr
        755                 760                 765

Pro Thr Pro Val Ile Trp Thr Pro Leu Ile Gln Ala Pro Leu Gln Ala
        770                 775                 780

Ala Ala Ala Thr Thr Ser Val Ala Ile Ala Leu Thr His His Pro Arg
785                 790                 795                 800

Leu Pro Ala Ala Ile Phe Arg Pro Pro Gly Ser Gly Leu Gly Asn
                805                 810                 815

Leu Gly Ala Gly Gln Thr Pro Arg His Leu Lys Arg Leu Gln Ser Leu
                820                 825                 830

Ile Pro Ser Ala Leu Gly Ser Ala Ser Pro Ala Ser Ser Pro Ser Gln
        835                 840                 845

Val Asp Thr Pro Ser Ser Ser Phe His Ile Gln Gln Leu Ala Gly
        850                 855                 860

Phe Ser Ala Pro Ala Gly Leu Ser Pro Leu Leu Pro Ser Ser Ser Ser
865                 870                 875                 880

Ser Pro Pro Pro Gly Ala Cys Gly Ser Pro Ala Pro Thr Pro Ser
                885                 890                 895

Ala Gly Val Ala Ala Thr Thr Ile Ala Gly Phe Gly His Phe His Lys
                900                 905                 910

Ala Leu Gly Gly Ser Leu Ser Ser Ser Asp Ser Pro Leu Leu Thr Pro
        915                 920                 925

Leu Gln Pro Gly Ala Arg Ser Pro Gln Ala Ala Gln Pro Ser Pro Ala
        930                 935                 940

Pro Pro Gly Ala Arg Gly Gly Leu Gly Leu Pro Glu His Phe Leu Pro
945                 950                 955                 960

Pro Pro Pro Ser Ser Arg Ser Pro Ser Ser Pro Gly Gln Leu Gly
                965                 970                 975

Gln Pro Pro Gly Glu Leu Ser Leu Gly Leu Ala Thr Gly Pro Leu Ser
                980                 985                 990

Thr Pro Glu Thr Pro Pro Arg Gln Pro Glu Pro Pro Ser Leu Val Ala
        995                 1000                1005

Gly Ala Ser Gly Gly Ala Ser Pro Val Gly Phe Thr Pro Arg Gly Gly
```

-continued

```
              1010                1015                1020
Leu Ser Pro Pro Gly His Ser Pro Gly Pro Pro Arg Thr Phe Pro Ser
       1025                1030                1035                1040
Ala Pro Pro Arg Ala Ser Gly Ser His Gly Ser Leu Leu Leu Pro Pro
                1045                1050                1055
Ala Ser Ser Pro Pro Pro Pro Gln Val Pro Gln Arg Arg Gly Thr Pro
                1060                1065                1070
Pro Leu Thr Pro Gly Arg Leu Thr Gln Asp Leu Lys Leu Ile Ser Ala
            1075                1080                1085
Ser Gln Pro Ala Leu Pro Gln Asp Gly Ala Gln Thr Leu Arg Arg Ala
       1090                1095                1100
Ser Pro His Ser Ser Gly Glu Ser Met Ala Ala Phe Pro Leu Phe Pro
  1105                1110                1115                1120
Arg Ala Gly Gly Gly Ser Gly Gly Ser Gly Ser Ser Gly Gly Leu Gly
                1125                1130                1135
Pro Pro Gly Arg Pro Tyr Gly Ala Ile Pro Gly Gln His Val Thr Leu
            1140                1145                1150
Pro Arg Lys Thr Ser Ser Gly Ser Leu Pro Pro Pro Leu Ser Leu Phe
       1155                1160                1165
Gly Ala Arg Ala Thr Ser Ser Gly Gly Pro Pro Leu Thr Ala Gly Pro
    1170                1175                1180
Gln Arg Glu Pro Gly Ala Arg Pro Glu Pro Val Arg Ser Lys Leu Pro
  1185                1190                1195                1200
Ser Asn Leu

<210> SEQ ID NO 4
<211> LENGTH: 5065
<212> TYPE: DNA
<213> ORGANISM: Homo sapiens

<400> SEQUENCE: 4
ggtcgctggg ctccgctcgg ttgcggcggg agccccggga cgggccggac gggccggggc      60
agaggaggcg aggcgagctc gcgggtggcc agccacaaag cccgggcggc gagacagacg     120
gacagccagc cctcccgcgg gacgcacgcc cggacccgc gcgggccgtg cgctctgcac      180
tccggagcgg ttccctgagc gccgcggccg cagagcctct ccggccggcg cccattgttc     240
cccgcggggg cggggcgcct ggagccgggc ggcgcgccgc gccctgaac gccagaggga      300
gggagggagg caagaaggga gcgcggggtc cccgcgccca gccgggcccg ggaggaggtg     360
tagcgcggcg agcccgggga ctcggagcgg gactaggatc ctccccgcgg cgcgcagcct     420
gcccaagcat gggcgcctga ggctgccccc acgccggcgg caaaggacgc gtccccacgg    480
gcggactgac cggcgggcgg acctggagcc cgtccgcggc gccgcgctcc tgccccggc     540
ccggtccgac cccggccccct ggcgccatgg acaagctgcc gccgtccatg cgcaagcggc   600
tctacagcct cccgcagcag gtgggggcca aggcgtggat catggacgag aagaggacg     660
ccgaggagga ggggggccggg ggccgccaag accccagccg caggagcatc cggctgcggc  720
cactgccctc gccctccccc tcggcggccg cgggtggcac ggagtcccgg agctcggccc    780
tcggggcagc ggacagcgaa gggcggcc gcggcgcggg caagtccagc acgaacggcg      840
actgcaggcg cttccgcggg agcctggcct cgctgggcag ccggggcggc ggcagcggcg    900
gcacggggag cggcagcagt cacgacacc tgcatgactc cgcggaggag cggcggctca     960
tcgccgaggg cgacgcgtcc cccggcgagg acaggacgcc cccaggcctg gcggccgagc   1020
```

-continued

```
ccgagcgccc cggcgcctcg gcgcagcccg cagcctcgcc gccgccgccc cagcagccac    1080
cgcagccggc ctccgcctcc tgcgagcagc cctcggtgga caccgctatc aaagtggagg    1140
gaggcgcggc tgccggcgac cagatcctcc cggaggccga ggtgcgcctg ggccaggccg    1200
gcttcatgca gcgccagttc ggggccatgc tccaacccgg ggtcaacaaa ttctccctaa    1260
ggatgttcgg cagccagaaa gccgtggagc gcgaacagga gagggtcaag tcggccggat    1320
tttggattat ccacccctac agtgacttca gattttactg ggacctgacc atgctgctgc    1380
tgatggtggg aaacctgatt atcattcctg tgggcatcac cttcttcaag gatgagaaca    1440
ccacaccctg gattgtcttc aatgtggtgt cagacacatt cttcctcatc gacttggtcc    1500
tcaacttccg cacagggatc gtggtggagg acaacacaga gatcatcctg acccgcagc    1560 ggattaaaat gaagtacctg aaaagctggt tcatggtaga tttcatttcc tccatccccg    1620
tggactacat cttcctcatt gtggagacac gcatcgactc ggaggtctac aagactgccc    1680
gggccctgcg cattgtccgc ttcacgaaga tcctcagcct cttacgcctg ttacgcctct    1740
cccgcctcat tcgatatatt caccagtggg aagagatctt ccacatgacc tacgacctgg    1800
ccagcgccgt ggtgcgcatc gtgaacctca tcggcatgat gctcctgctc tgccactggg    1860
acggctgcct gcagttcctg gtacccatgc tacaggactt ccctgacgac tgctgggtgt    1920
ccatcaacaa catggtgaac aactcctggg ggaagcagta ctcctacgcg ctcttcaagg    1980
ccatgagcca catgctgtgc atcggctacg gcggcaggc gccgtgggc atgtccgacg    2040 tctggctcac catgctcagc atgatcgtgg gtgccacctg ctacgccatg ttcattggcc    2100
acgccactgc cctcatccag tccctggact cctcccggcg ccagtaccag gaaaagtaca    2160
agcaggtgga gcagtacatg tcctttcaca agctcccgcc cgacacccgg cagcgcatcc    2220
acgactacta cgagcaccgc taccagggca agatgttcga cgaggagagc atcctgggcg    2280
agctaagcga gccctgcgg gaggagatca tcaactttaa ctgtcggaag ctggtggcct    2340
ccatgccact gtttgccaat gcggaccca acttcgtgac gtccatgctg accaagctgc    2400
gtttcgaggt cttccagcct ggggactaca tcatccggga aggcaccatt ggcaagaaga    2460
tgtacttcat ccagcatggc gtggtcagcg tgctcaccaa gggcaacaag gagaccaagc    2520
tggccgacgg ctcctacttt ggagagatct gcctgctgac ccggggccgg cgcacagcca    2580
gcgtgagggc cgacacctac tgccgcctct actcgctgag cgtggacaac ttcaatgagg    2640
tgctggagga gtaccccatg atgcgaaggg ccttcgagac cgtggcgctg gaccgcctgg    2700
accgcattgg caagaagaac tccatcctcc tccacaaagt ccagcacgac ctcaactccg    2760
gcgtcttcaa ctaccaggag aatgagatca tccagcagat tgtgcagcat gaccgggaga    2820
tggcccactg cgcgcaccgc gtccaggctg ctgcctctgc caccccaacc ccacgcccg    2880 tcatctggac cccgctgatc caggcaccac tgcaggctgc cgctgccacc acttctgtgg    2940
ccatagccct cacccaccac cctcgcctgc ctgctgccat cttccgccct ccccaggat    3000 ctgggctggg caacctcggt gccgggcaga cgccaaggca cctgaaacgg ctgcagtccc    3060
tgatcccttc tgcgctgggc tccgcctcgc ccgccagcag cccgtcccag gtggacacac    3120
cgtcttcatc ctccttccac atccaacagc tggctggatt ctctgccccc gctggactga    3180
gcccactcct gccctcatcc agctcctccc cacccccgg ggcctgtggc tcccctcgg    3240 ctcccacacc atcagctggc gtagccgcca ccaccatagc cgggtttggc cacttccaca    3300
aggcgctggg tggctccctg tcctcctccg actctcccct gctcacccg ctgcagccag    3360 gcgcccgctc cccgcaggct gcccagccat ctcccgcgcc accgggcc cggggaggcc    3420
```

-continued

```
tgggactccc ggagcacttc ctgccacccc caccctcatc cagatccccg tcatctagcc    3480
ccgggcagct gggccagcct cccggggagt tgtccctagg tctggccact ggcccactga    3540
gcacgccaga cacccccca cggcagcctg agccgccgtc ccttgtggca ggggcctctg     3600 gggggcttc ccctgtaggc tttactcccc gaggaggtct cagcccccct ggccacagcc     3660
caggcccccc aagaaccttc ccgagtgccc cgccccgggc ctctggctcc cacggatcct    3720
tgctcctgcc acctgcatcc agcccccac cacccccaggt ccccagcgc cggggcacac     3780 ccccgctcac ccccggccgc ctcacccagg acctcaagct catctccgcg tctcagccag    3840
ccctgcctca ggacggggcg cagactctcc gcagagcctc cccgcactcc tcaggggagt    3900
ccatggctgc cttcccgctc ttccccaggg ctggggtgg cagcggggc agtgggagca      3960 gcgggggcct cggtccccct gggaggccct atggtgccat cccggccag cacgtcactc     4020 tgcctcggaa gacatcctca ggttctttgc caccccctct gtctttgttt ggggcaagag    4080
ccacctcttc tgggggggccc cctctgactg ctggaccca gagggaacct ggggccaggc   4140
ctgagccagt gcgctccaaa ctgccatcca atctatgagc tgggcccttc cttccctctt    4200
ctttcttctt ttctctccct tccttcttcc ttcaggttta actgtgatta ggagatatac    4260
caataacagt aataattatt taaaaaacca cacacaccag aaaaacaaaa gacagcagaa    4320
aataaccagg tattcttaga gctatagatt tttggtcact tgcttttata gactatttta    4380
atactcagca ctagagggag ggaggggag ggaggaggga gcaggcaggt cccaaatgca    4440
aaagccagag aaaggcagat ggggtctccg gggctgggca ggggtgggag tggccagtgt    4500
tggcggttct tagagcagat gtgtcattgt gttcatttag agaaacagct gccatcagcc    4560
cgttagctgt aacttggagc tccactctgc ccccagaaag gggctgccct ggggtgtgcc    4620
ctggggagcc tcagaagcct gcgaccttgg gagaaaaggg ccagggccct gagggcctag    4680
cattttttct actgtaaacg tagcaagatc tgtatatgaa tatgtatatg tatatgtatg    4740
taagatgtgt atatgtatag ctatgtagcg ctctgtagag ccatgtagat agccactcac    4800
atgtgcgcac acgtgtgcgg tctagtttaa tcccatgttg acaggatgcc caggtcacct    4860
tacacccagc aacccgcctt ggcccgcagg ctgtgcactg catggtctag ggacgttctc    4920
tctccagtcc tcagggaaga ggacgccagg acttcgcagc aggcccctc tctccccatc    4980 tctggtctca aagccagtcc cagcctgacc tctcaccaca cggaagtgga agactcccct    5040
ttcctagggc ctcaagcaca caccg                                         5065
```

<210> SEQ ID NO 5
<211> LENGTH: 863
<212> TYPE: PRT
<213> ORGANISM: Murinae gen. sp.

<400> SEQUENCE: 5

```
Met Asp Ala Arg Gly Gly Gly Arg Pro Gly Asp Ser Pro Gly Thr
 1               5                  10                  15

Thr Pro Ala Pro Gly Pro Pro Pro Pro Pro Pro Ala Pro Pro
            20                  25                  30

Gln Pro Gln Pro Pro Ala Pro Pro Asn Pro Thr Thr Pro Ser
        35                  40                  45

His Pro Glu Ser Ala Asp Glu Pro Gly Pro Arg Ala Arg Leu Cys Ser
    50                  55                  60

Arg Asp Ser Ala Cys Thr Pro Gly Ala Ala Lys Gly Gly Ala Asn Gly
65                  70                  75                  80
```

-continued

```
Glu Cys Gly Arg Gly Glu Pro Gln Cys Ser Pro Glu Gly Pro Ala Arg
                85                  90                  95
Gly Pro Lys Val Ser Phe Ser Cys Arg Gly Ala Ala Ser Gly Pro Ser
            100                 105                 110
Ala Ala Glu Glu Ala Gly Ser Glu Ala Gly Pro Ala Gly Glu Pro
        115                 120                 125
Arg Gly Ser Gln Ala Ser Phe Leu Gln Arg Gln Phe Gly Ala Leu Leu
    130                 135                 140
Gln Pro Gly Val Asn Lys Phe Ser Leu Arg Met Phe Gly Ser Gln Lys
145                 150                 155                 160
Ala Val Glu Arg Glu Gln Glu Arg Val Lys Ser Ala Gly Ala Trp Ile
                165                 170                 175
Ile His Pro Tyr Ser Asp Phe Arg Phe Tyr Trp Asp Phe Thr Met Leu
            180                 185                 190
Leu Phe Met Val Gly Asn Leu Ile Ile Ile Pro Val Gly Ile Thr Phe
        195                 200                 205
Phe Lys Asp Glu Thr Thr Ala Pro Trp Ile Val Phe Asn Val Val Ser
    210                 215                 220
Asp Thr Phe Phe Leu Met Asp Leu Val Leu Asn Phe Arg Thr Gly Ile
225                 230                 235                 240
Val Ile Glu Asp Asn Thr Glu Ile Ile Leu Asp Pro Glu Lys Ile Lys
                245                 250                 255
Lys Lys Tyr Leu Arg Thr Trp Phe Val Val Asp Phe Val Ser Ser Ile
            260                 265                 270
Pro Val Asp Tyr Ile Phe Leu Ile Val Glu Lys Gly Ile Asp Ser Glu
        275                 280                 285
Val Tyr Lys Thr Ala Arg Ala Leu Arg Ile Val Arg Phe Thr Lys Ile
    290                 295                 300
Leu Ser Leu Leu Arg Leu Leu Arg Leu Ser Arg Leu Ile Arg Tyr Ile
305                 310                 315                 320
His Gln Trp Glu Glu Ile Phe His Met Thr Tyr Asp Leu Ala Ser Ala
                325                 330                 335
Val Met Arg Ile Cys Asn Leu Ile Ser Met Met Leu Leu Leu Cys His
            340                 345                 350
Trp Asp Gly Cys Leu Gln Phe Leu Val Pro Met Leu Gln Asp Phe Pro
        355                 360                 365
Ser Asp Cys Trp Val Ser Ile Asn Asn Met Val Asn His Ser Trp Ser
    370                 375                 380
Glu Leu Tyr Ser Phe Ala Leu Phe Lys Ala Met Ser His Met Leu Cys
385                 390                 395                 400
Ile Gly Tyr Gly Arg Gln Ala Pro Glu Ser Met Thr Asp Ile Trp Leu
                405                 410                 415
Thr Met Leu Ser Met Ile Val Gly Ala Thr Cys Tyr Ala Met Phe Ile
            420                 425                 430
Gly His Ala Thr Ala Leu Ile Gln Ser Leu Asp Ser Ser Arg Arg Gln
        435                 440                 445
Tyr Gln Glu Lys Tyr Lys Gln Val Glu Gln Tyr Met Ser Phe His Lys
    450                 455                 460
Leu Pro Ala Asp Phe Arg Gln Lys Ile His Asp Tyr Tyr Glu His Arg
465                 470                 475                 480
Tyr Gln Gly Lys Met Phe Asp Glu Asp Ser Ile Leu Gly Glu Leu Asn
                485                 490                 495
```

```
Gly Pro Leu Arg Glu Ile Val Asn Phe Asn Cys Arg Lys Leu Val
            500                 505                 510

Ala Ser Met Pro Leu Phe Ala Asn Ala Asp Pro Asn Phe Val Thr Ala
            515                 520                 525

Met Leu Thr Lys Leu Lys Phe Glu Val Phe Gln Pro Gly Asp Tyr Ile
            530                 535                 540

Ile Arg Glu Gly Thr Ile Gly Lys Lys Met Tyr Phe Ile Gln His Gly
545                 550                 555                 560

Val Val Ser Val Leu Thr Lys Gly Asn Lys Glu Met Lys Leu Ser Asp
            565                 570                 575

Gly Ser Tyr Phe Gly Glu Ile Cys Leu Leu Thr Arg Gly Arg Arg Thr
            580                 585                 590

Ala Ser Val Arg Ala Asp Thr Tyr Cys Arg Leu Tyr Ser Leu Ser Val
            595                 600                 605

Asp Asn Phe Asn Glu Val Leu Glu Glu Tyr Pro Met Met Arg Arg Ala
            610                 615                 620

Phe Glu Thr Val Ala Ile Asp Arg Leu Asp Arg Ile Gly Lys Lys Asn
625                 630                 635                 640

Ser Ile Leu Leu His Lys Val Gln His Asp Leu Ser Ser Gly Val Phe
            645                 650                 655

Asn Asn Gln Glu Asn Ala Ile Ile Gln Glu Ile Val Lys Tyr Asp Arg
            660                 665                 670

Glu Met Val Gln Gln Ala Glu Leu Gly Gln Arg Val Gly Leu Phe Pro
            675                 680                 685

Pro Pro Pro Pro Gln Val Thr Ser Ala Ile Ala Thr Leu Gln Gln
            690                 695                 700

Ala Val Ala Met Ser Phe Cys Pro Gln Val Ala Arg Pro Leu Val Gly
705                 710                 715                 720

Pro Leu Ala Leu Gly Ser Pro Arg Leu Val Arg Arg Ala Pro Pro Gly
            725                 730                 735

Pro Leu Pro Pro Ala Ala Ser Pro Gly Pro Pro Ala Ala Ser Pro Pro
            740                 745                 750

Ala Ala Pro Ser Ser Pro Arg Ala Pro Arg Thr Ser Pro Tyr Gly Val
            755                 760                 765

Pro Gly Ser Pro Ala Thr Arg Val Gly Pro Ala Leu Pro Ala Arg Arg
770                 775                 780

Leu Ser Arg Ala Ser Arg Pro Leu Ser Ala Ser Gln Pro Ser Leu Pro
785                 790                 795                 800

His Gly Val Pro Ala Pro Ser Pro Ala Ala Ser Ala Arg Pro Ala Ser
            805                 810                 815

Ser Ser Thr Pro Arg Leu Gly Pro Ala Pro Thr Ala Arg Thr Ala Ala
            820                 825                 830

Pro Ser Pro Asp Arg Arg Asp Ser Ala Ser Pro Gly Ala Ala Ser Gly
            835                 840                 845

Leu Asp Pro Leu Asp Ser Ala Arg Ser Arg Leu Ser Ser Asn Leu
            850                 855                 860

<210> SEQ ID NO 6
<211> LENGTH: 3102
<212> TYPE: DNA
<213> ORGANISM: Murinae gen. sp.

<400> SEQUENCE: 6
ccgctccgct ccgcactgcc cggcgccgcc tcgccatgga tgcgcgcggg ggcggcgggc        60
```

-continued

| | |
|---|---|
| ggccgggcga tagtccgggc acgaccsctg cgccggggcc gccgccaccg ccgccgccgc | 120 |
| ccgcgccccc tcagcctcag ccaccacccg cgccaccccg aaccccacg acccsctcgc | 180 |
| acccggagtc ggcggacgag cccggcccgc gcgcccggct ctgcagccgc gacagcgcct | 240 |
| gcacccctgg cgcggccaag ggcggcgcga atggcgagtg cggggcgcggg gagccgcagt | 300 |
| gcagccccga gggccccgcg cgcggcccca aggtttcgtt ctcatgccgc ggggcggcct | 360 |
| ccgggccctc ggcggccgag gaggcgggca gcgaggaggc gggcccggcg ggtgagccgc | 420 |
| gcggcagcca ggctagcttc ctgcagcgcc aattcggggc gcttctgcag cccggcgtca | 480 |
| acaagttctc cctgcggatg ttcggcagcc agaaggccgt ggagcgcgag caggaacgcg | 540 |
| tgaagtcggc gggggcctgg atcatccacc cctacagcga cttcaggttc tactgggact | 600 |
| tcaccatgct gttgttcatg gtgggaaatc tcattatcat tcccgtgggc atcactttct | 660 |
| tcaaggacga gaccaccgcg ccctggatcg tcttcaacgt ggtctcggac actttcttcc | 720 |
| tcatggactt ggtgttgaac ttccgcaccg gcattgttat tgaggacaac acggagatca | 780 |
| tcctggaccc cgagaagata aagaagaagt acttgcgtac gtggttcgtg gtggacttcg | 840 |
| tgtcatccat cccggtggac tacatcttcc tcatagtgga aagggaatc gactccgagg | 900 |
| tctacaagac agcgcgtgct ctgcgcatcg tgcgcttcac caagatcctc agtctgctgc | 960 |
| ggctgctgcg gctatcacgg ctcatccgat atatccacca gtgggaagag attttccaca | 1020 |
| tgacctacga cctggcaagt gcagtgatgc gcatctgtaa cctgatcagc atgatgctac | 1080 |
| tgctctgcca ctgggacggt tgcctgcagt tcctggtgcc catgctgcaa gacttcccca | 1140 |
| gcgactgctg ggtgtccatc aacaacatgg tgaaccactc gtggagcgag ctctactcgt | 1200 |
| tcgcgctctt caaggccatg agccacatgc tgtgcatcgg ctacggcgg caggcgcccg | 1260 |
| agagcatgac agacatctgg ctgaccatgc tcagcatgat cgtaggcgcc acctgctatg | 1320 |
| ccatgttcat tgggcacgcc actgcgctca tccagtccct ggattcgtca cggcgccaat | 1380 |
| accaggagaa gtacaagcaa gtagagcaat acatgtcctt ccacaaactg cccgctgact | 1440 |
| tccgccagaa gatccacgat tactatgaac accggtacca agggaagatg tttgatgagg | 1500 |
| acagcatcct tggggaactc aacgggccac tgcgtgagga gattgtgaac ttcaactgcc | 1560 |
| ggaagctggt ggcttccatg ccgctgtttg ccaatgcaga ccccaacttc gtcacagcca | 1620 |
| tgctgacaaa gctcaaattt gaggtcttcc agcctggaga ttacatcatc cgagagggga | 1680 |
| ccatcgggaa gaagatgtac ttcatccagc atgggggtgt gagcgtgctc accaagggca | 1740 |
| acaaggagat gaagctgtcg gatggctcct atttcgggga gatctgcttg ctcacgaggg | 1800 |
| gccggcgtac ggccagcgtg cgagctgaca cctactgtcg cctctactca ctgagtgtgg | 1860 |
| acaatttcaa cgaggtgctg gaggaatacc ccatgatgcg gcgtgccttt gagactgtgg | 1920 |
| ctattgaccg gctagatcgc ataggcaaga agaactccat cttgctgcac aaggttcagc | 1980 |
| atgatctcag ctcaggtgtg ttcaacaacc aggagaatgc catcatccag gagattgtca | 2040 |
| aatatgaccg tgagatggtg cagcaggcag agcttggcca gcgtgtgggg ctcttcccac | 2100 |
| caccgccacc accgcaggtc acatcggcca ttgccaccct acagcaggct gtggccatga | 2160 |
| gcttctgccc gcaggtggcc cgcccgctcg tggggcccct ggcgctaggc tccccacgcc | 2220 |
| tagtgcgccc cgcgccccca gggcctctgc tcctgcagc ctcgcagggg ccaccgcag | 2280 |
| caagccccc ggctgcaccc tcgagccctc gggcaccgcg gacctcaccc tacggtgtgc | 2340 |
| ctggctctcc ggcaacgcgc gtggggcccg cattgcccgc acgtcgcctg agccgcgcct | 2400 |
| cgcgcccact gtccgcctcg cagccctcgc tgccccatgg cgtgcccgcg cccagcccg | 2460 |

```
cggcctctgc gcgcccggcc agcagctcca cgccgcgcct gggacccgca cccaccgccc    2520
ggaccgccgc gcccagtccg gaccgcaggg actcagcctc gccgggcgct gccagtggcc    2580
tcgacccact ggactctgcg cgctcgcgcc tctcttccaa cttgtgaccc ttgagcgccg    2640
ccccgcgggc cggcgggc cgtcatccac accaaagcca tgcctcgcgc cgcccgcccg      2700
tgcccgtgca gaagccatag agggacgtag gtagcttagg aggcgggcgg ccctgcgccc    2760
ggctgtcccc ccatcgccct cgcccaccc ccatcgcccc tgcccagcg gcggccgcac      2820 gggagaggga ggggtgcgat cacctcggtg cctcagcccc aacctgggac agggacaggg    2880
cggccctggc cgaggacctg gctgtgcccc gcatgtgcgg tggcctccga ggaagaatat    2940
ggatcaagtg caatacacgg ccaagccggc gtgggggtga ggctgggtcc ccggccgtcg    3000
ccatgaatgt actgacgagc cgaggcagca gtggcccca cgcccattaa acccacaacc     3060
ccattccgcg caataaacga cagcattggc aaaaaaaaaa aa                       3102
```

<210> SEQ ID NO 7
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Description of Artificial Sequence:Primer

<400> SEQUENCE: 7
gccaatacca ggagaag                                                     17

<210> SEQ ID NO 8
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Description of Artificial Sequence:Primer

<400> SEQUENCE: 8
tgagtagagg cgacagtag                                                   19

<210> SEQ ID NO 9
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Description of Artificial Sequence:Primer

<400> SEQUENCE: 9
agtggcctcg acccactgga ctct                                             24

<210> SEQ ID NO 10
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Description of Artificial Sequence:Primer

<400> SEQUENCE: 10
ccgcctccta agctacctac gtccc                                            25

PROCESS FOR IDENTIFYING SUBSTANCES WHICH MODULATE THE ACTIVITY OF HYPERPOLARIZATION-ACTIVATED CATION CHANNELS

This is a continuation of application Ser. No. 09/779,587, filed Feb. 9, 2001, now abandoned, which is incorporated herein by reference.

BACKGROUND OF THE INVENTION

1. Field of the Invention

The present invention relates to the field of biological cell-to-cell communication and electrochemical signalling between biological cells. In particular, the present invention provides a process for identifying substances that modulate the activity of hyperpolarization-activated cation channels, and the use of this process.

2. Description of the Relevant Art

Some genes of murine and human hyperpolarization-activated cation channels are already known. Examples include muHCN2(muHAC1) (Ludwig et al. (1998)), huHCN4 (Ludwig et al. (1999)), huHCN2 (Vaccari, T. et al. (1999) Biochim. Biophys. Acta 1446(3): 419–425), and those disclosed in WO 99/32615 and WO 99/42574. See, also, Tables 1–6 herein.

Ludwig et al. (1998) have shown that muHCN2 can be transfected transiently in HEK293 cells, and that the corresponding channel in the transfected cells can be examined easily by electrophysiological methods (patch-clamp studies). The electrophysiological properties of the cloned channel correspond to the $l_f$ or $l_h$ current described in pacemaker cells, which had hitherto not been known on a molecular level (Ludwig et al. (1998), Biel et al. (1999)). The channel activates when the holding potential is changed toward hyperpolarization (potential at about B100 to B160 mV). However, the patch-clamp technique cannot be automated and is not suitable for high-throughput screening (HTS).

Using suitable dyes, ion currents can be measured in an FLIPR (fluorescence imaging plate reader; Molecular Devices, Sunnyvale Calif., USA). Influx or efflux of ions leads to changes in the membrane potential, which can be measured in high-throughput screening in an FLIPR using suitable fluorescent dyes. However, in contrast to the patch-clamp method, it is not possible to generate voltage changes in the FLIPR. Voltage changes are, however, an essential prerequisite for the activation of hyperpolarization-activated cation channels.

SUMMARY OF THE INVENTION

For the examination of the largest possible number of substances, we have developed a process that permits, among other things, high-throughput screening (HTS) for modulators of a hyperpolarization-activated cation channel.

DETAILED DESCRIPTION OF THE INVENTION

Abbreviations used herein are listed in Table 7 below.

The present invention provides a way to hyperpolarize cells that express a hyperpolarization-activated cation channel (i.e. to activate the hyperpolarization-activated cation channel) and to maintain this hyperpolarization of the cell, for example, until a measurement of membrane potential can be taken. Under physiological conditions, a hyperpolarization of the cell that is sufficient to activate a hyperpolarization-activated cation channel is reversed by the activity of that channel. Only when hyperpolarization can be maintained is it possible to measure, for example in an FLIPR, the depolarization of the cell caused under suitable conditions by a substance that modulates the activity of the hyperpolarization-activated cation channel.

Generally speaking, the present invention provides a process for examining hyperpolarization-activated cation channels. In the process, cells that express the hyperpolarization-activated cation channels are hyperpolarized (i.e. the hyperpolarization-activated cation channel is activated) and this hyperpolarization of the cells, which is reversed under physiological conditions by the activity of the hyperpolarization-activated cation channel, is maintained. By exclusion of extracellular sodium ions, the activated channel is unable to transport sodium ions into the cells, i.e. to depolarize the cells. If, simultaneously or even prior to the addition of the sodium ions, substances are added that modulate the activity of the hyperpolarization-activated cation channel, the depolarization is affected. For example, compared to when only sodium ions are added, depolarization is increased in the case of HCN activators (for example forskolin) and reduced in the case of HCN inhibitors (for example zatebradine=3-[3-[[2-(3,4-dimethoxyphenyl)ethyl]methylamino]propyl]-1,3,4,5-tetrahydro-7,8-dimethoxy-2H-3-benzazepin-2-one; Reiffen et al. (1990)).

By measuring the depolarization of the cells or the changes of their membrane potential, it is possible to identify substances that modulate the activity of the hyperpolarization-activated cation channel.

In one aspect, the invention generally provides a process for identifying substances that modulate the activity of hyperpolarization-activated cation channels, wherein a) cells which express a hyperpolarization-activated cation channel are used;

b) the cells are hyperpolarized in the presence of a potential-sensitive fluorescent dye using an isoosmolar sodium-ion-free buffer; and c) the change in the membrane potential of the cells following simultaneous addition of sodium ions and the substance to be examined is detected and recorded.

Thus, in embodiments, the invention provides a process for identifying substances that modulate the activity of hyperpolarization-activated cation channels, wherein the process comprises a) providing, in a suitable container, cells that express a hyperpolarization-activated cation channel;

b) hyperpolarizing the cells in the presence of a potential-sensitive fluorescent dye and an isoosmolar sodium-ion-free buffer;

c) optionally, determining the membrane potential of the cells;

d) simultaneously adding sodium ions and a sample containing at least one substance to be tested for its ability to modulate the activity of the cation channel;

e) determining the membrane potential of the cells;

f) determining whether the membrane potential changed upon simultaneous addition of sodium ions and the substance(s); and g) optionally, recording the change in membrane potential, wherein a change in membrane potential indicates the presence of at least one substance in the sample that modulates the activity of the cation channel.

A suitable container is any container, vessel, receptacle, etc. that can be used to hold the reagents and samples to be used in the assay. Suitable containers are disclosed in, or identifiable from, literature provided by manufacturers of equipment designed to determine membrane potentials. Such equipment is publicly available and well known to those of skill in the art.

In embodiments where step "c)" is not performed, a parallel assay, using the same strain of cells at the same concentration in the same assay composition, can be run to determine the membrane potential of the cells in the absence of the sample suspected of containing at least one substance that can modulate the activity of a cation channel.

In embodiments, the assay is a high-throughput assay.

In another aspect, the invention generally provides a process for identifying substances that modulate the activity of hyperpolarization-activated cation channels, wherein
a) cells which express a hyperpolarization-activated cation channel are used;
b) the cells are hyperpolarized in the presence of a potential-sensitive fluorescent dye using an isoosmolar sodium-ion-free buffer;
c) the cells are incubated with a substance to be examined; and
d) the change in the membrane potential of the cells after addition of sodium ions is detected and recorded.

Thus, in embodiments, the invention provides a process for identifying substances that modulate the activity of hyperpolarization-activated cation channels, wherein the process comprises
a) providing, in a suitable container, cells that express a hyperpolarization-activated cation channel;
b) hyperpolarizing the cells in the presence of a potential-sensitive fluorescent dye and an isoosmolar sodium-ion-free buffer;
c) optionally, determining the membrane potential of the cells;
d) incubating the cells with a sample containing at least one substance to be tested for its ability to modulate the activity of the cation channel;
e) optionally, determining the membrane potential of the cells;
f) optionally, determining whether the membrane potential changed upon addition of the substance(s) to be tested;
g) adding sodium ions;
h) determining the membrane potential of the cells;
i) determining whether the membrane potential changed upon addition of the sodium ions; and
j) optionally, recording the change in membrane potential, wherein a change in membrane potential between the time before the sodium ions are added and after the sodium ions are added indicates the presence of at least one substance in the sample that modulates the activity of the cation channel.

Extracellular potassium ions can be included in the assay. In certain situations, these ions can improve the function of the hyperpolarization-activation cation channels. For example, they might be included when HCN (HAC) channels are being used in the process. Thus, in embodiments of the present invention, the isoosmolar sodium-ion-free buffer comprises potassium ions ($K^+$). In embodiments, the buffer comprises potassium ions in the form of potassium chloride. In embodiments, the buffer comprises potassium ions at a concentration of at least about 0.5 mM $K^+$. In embodiments, the buffer comprises potassium ions at a concentration of at least about 0.8 mM $K^+$. In embodiments, the buffer comprises potassium ions at a concentration of about 2 mM. In embodiments, the buffer comprises potassium ions at a concentration of about 5 mM.

In embodiments, the isoosmolar sodium-ion-free buffer comprises at least one cation that is not able to cross the membrane in amounts that correspond to the normal extracellular sodium ion concentration. For example, the buffer can comprise choline, for example in the form of choline chloride, or NMDG (N-methyl-D-glucamine). In embodiments, the isoosmolar sodium-ion-free buffer comprises both potassium ions and at least one cation that is not able to cross the membrane in amounts that correspond to the normal extracellular sodium ion concentration.

In embodiments, the isoosmolar sodium-ion-free buffer comprises a potential-sensitive dye, for example a potential-sensitive fluorescent dye. Included among these are oxonol derivatives, such as 3-bis-barbituric acid oxonol. Thus, in embodiments, the isoosmolar sodium-ion-free buffer comprises potassium ions, at least one cation that is not able to cross the membrane in amounts that correspond to the normal extracellular sodium ion concentration, and a potential-sensitive dye.

In embodiments, the buffer comprises potential-sensitive fluorescent dyes that are suitable for examining the membrane potential of nonexcitable cells. Examples of such dyes include, but are not limited to, potential-sensitive slow-response dyes. Non-limiting examples of such potential-sensitive slow-response dyes include bis-(1,3-dibutylbarbituric acid)trimethine oxonol [$DiBac_4(3)$], bis-(1,3-diethylthiobarbituric acid)trimethine oxonol [$DiSBac_2(3)$] or bis-(1,3-dibutylbarbituric acid)pentamethine oxonol [$DiBac_4(5)$]. Other known and suitable potential-sensitive dyes include, but are not limited to, fast-response dyes (for example, of the styrylpyridinium type), which are used in certain embodiments in conjunction with excitable cells, such as neurons, cardiac cells, etc. These potential-sensitive dyes react in the millisecond range and are not particularly sensitive (2–10% fluorescence change per 100 mV potential change). Other suitable dyes include slow-response dyes of the carbocyanine type. Non-limiting examples of these slow-response dyes include diOC5(3)-3,3'-dipentyloxacarbocyanine iodide, diOC6(3)-3,3'-dihexyloxacarbocyanine iodide, etc.), JC-1 (5,5',6,6'-tetrachloro-1,1'-3,3'-tetraethylbenzimidazolecarbocyanine iodide), and rhodamine 123. In embodiments, these slow-response potential-sensitive dyes are used in studies of the membrane potential of mitochondria.

One embodiment of the invention relates to the use of the fluorescent dye from the FLIPR Membrane Potential Assay Kit (Molecular Devices, Sunnyvale, Calif., USA). The fluorescence of this dye can be measured using a standard emission filter, which is transparent between about 510 and about 580 nm. In embodiments, fluorescence of this dye is measured using a filter that is transparent above about 550 nm. The manufacturer of this dye and kit disclose a number of advantages of their product, over, for example, assays based on $DiBac_4(3)$, and these advantages can be applicable to the present invention.

Some of these advantages include:
1) the measurement of membrane potentials with the kit is not temperature sensitive, in contrast to $DiBac_4(3)$, where the temperature has to be equilibrated prior to the actual measurement in the FLIPR;
2) the volume added in the FLIPR can be greater than that in the case of $DiBac_4(3)$, where usually all substances have to be added in a 10-fold concentrated form;
3) the measurements can be carried out much more rapidly, since the kit requires a much shorter time to reach the steady state than $DiBac_4(3)$, which usually requires between 10 and 30 minutes;
4) for many measurement protocols, a washing step prior to the addition of the dye is no longer required; and 5) the dye does not have to be present in each solution.

In embodiments of the present invention, the first two advantages are relied upon because these two advantages can be applied to assays of hyperpolarization-activated cation channels. The first two advantages can also be applied to embodiments of the invention that are directed to high-throughput screening, since screening of a large number of samples at once can be complicated and/or time consuming. For example, in embodiments where FLIPR II, which allows the measurement in 384-well plates and which is preferably employed for high-throughput screening thermostating, is used, these first two advantages can reduce the complications and time necessary to perform the assay process. In the case of poorly soluble substances, it is furthermore an advantage if they can be added to the cells in five-, three-, or even two-fold concentrated form instead of 10-fold concentrated form, as is typical with $DiBac_4(3)$.

In the processes of the present invention, cells having an elevated intracellular cAMP concentration can be used. Elevated intracellular cAMP concentrations can be achieved, for example, by adding cAMP derivatives that are able to cross the membrane. Non-limiting examples of such derivatives include dibutyryl-cAMP and 8-bromo-cAMP. As a further non-limiting example, the intracellular cAMP concentration can be increased by the addition of an adenylate cyclase activator, for example forskolin. When forskolin is used, successful results can be obtained when it is supplied in concentrations of less than about 100 $\mu$M. For example, forskolin can be used at a concentration of between about 1 $\mu$M and about 100 $\mu$M. It can also be used at concentrations less than about 1 $\mu$M. In embodiments, it is used at a concentration of about 10 $\mu$M. In principle, it is also possible to use all substances or ligands that activate adenylate cyclase by signal transduction in the cell line employed (for example ligands for b-adrenergic receptors, such as adrenalin, isoproterenol, noradrenalin, etc., if the cell has endogenous b-adrenergic receptors).

To depolarize the membrane potential, $Na^+$ (which can be supplied in the form of NaCl, for example) is added in the FLIPR to the cells which have hyperpolarized by the sodium-ion-free buffer. In embodiments, the $Na^+$ is added to achieve a final $Na^+$ concentration of about 20–100 mM. In embodiments, it is added to achieve a final $Na^+$ concentration of about 50 mM. In embodiments where the FLIPR Membrane Potential Assay Kit (Molecular Devices, Sunnyvale, Calif., USA) is used, the final $Na^+$ concentration can be about 20–100 mM. For example, it can be about 40–80 mM.

In embodiments, the invention relates to processes in which the hyperpolarization-activatable cation channel is an HCN1, HCN2, HCN3, HCN4 channel (where HAC1=HCN2, HAC2=HCN1, HAC3=HCN3 and HAC4=HCN4) or a KAT1 (=AKT) channel (hyperpolarization-activated potassium channel from Arabidopsis thaliana); a heteromultimer of these channels (i.e. a channel which is composed of subunits of different hyperpolarization-activated cation channels); or a chimeric hyperpolarization-activated cation channel (i.e. a synthetic channel in which individual subunits are composed of parts of different channels or hyperpolarization-activated cation channels). The hyperpolarization-activated cation channel is preferably a human hyperpolarization-activated cation channel, for example huHCN2, (SEQ ID NO. 1, SEQ ID NO. 2) or huHCN4 (SEQ ID NO. 3, SEQ ID NO. 4), or a murine hyperpolarization-activated cation channel muHCN2 (SEQ ID NO. 5, SEQ ID NO. 6). See Tables 1–6. On the amino acid level, the identity between muHCN2 and huHCN2 is 94.8%. In principle, the process is suitable for all cation channels which are activated by hyperpolarization. For example, it is suitable for HCN1–4 (or HAC1–4; see Biel et al. (1999)).

The cells can be any eukaryotic cells. For example, the cells can be mammalian cells, such as CHO or HEK293 cells. In embodiments, CHO cells or another cell line having comparably few endogenous potassium channels are used, since endogenous potassium channels might interfere with the measurement, for example, in the FLIPR. In other embodiments cells whose endogenous potassium channels are not functionally expressed (for example the corresponding knock-out cells) are used.

The cells can, but do not necessarily, contain nucleic acids (i.e., RNA, DNA, PNA) that code for the hyperpolarization-activated cation channel. In embodiments, the cells contain DNA. In embodiments, the cells contain RNA. In embodiments, the cells contain a eDNA of a hyperpolarization-activated cation channel in a suitable plasmid. Such cells can be prepared by transfecting the original cell line with a plasmid that contains the cDNA of a hyperpolarization-activated cation channel. Other techniques can be used as well. Techniques for introducing heterologous nucleic acids into cells are well known and widely practiced by those of skill in the art, and thus need not be detailed here.

In the case of the hyperpolarization-activated cation channels, it is an object of the invention to detect, and optionally, record changes in the membrane potential of the cells, where the changes are the result of the activation or the inhibition of these channels. Detection can utilize bis-barbituric acid oxonols. Three bis-barbituric acid oxonols (see, for example, "Handbook of Fluorescent Probes and Research Chemicals", 6th edition, Molecular Probes, Eugene Oreg., USA), which are mainly referred to as DiBac dyes, form a family of potential-sensitive dyes having excitation maxima at 490 nm ($DiBac_4(3)$), 530 nm ($DiSBac_2(3)$), and 590 nm ($DiBac_4(5)$). The dyes get into depolarized cells by binding to intracellular proteins or membranes, leading to increased fluorescence and a red shift. Hyperpolarization results in the expulsion of the anionic dyes and thus in a decrease in fluorescence. This decrease in fluorescence can be measured, for example, with the measuring device FLIPR. Accordingly, one embodiment of the invention relates to the measurement of the membrane potential in a Fluorescent Imaging Plate Reader (FLIPR).

The FLIPR (for: Fluorescent Imaging Plate Reader; Manufacturer: Molecular Devices, Sunnyvale, Calif., USA) is a measuring device that allows the simultaneous measurement of changes of the fluorescence intensity in all wells of a microtiter plate. The dyes used are excited at about 488 nm using an argon laser, which is integrated into the system. The standard emission filter of the system is transparent in the range from 510 B 580 nm. The emitted fluorescence is registered using a CCD camera, and the system permits the simultaneous recording, within an interval of about one second, of the fluorescence in all wells of a 96-well or 384-well microtiter plate. Using a built-in pipettor, it is even possible to determine the fluorescence during the addition of the substance, which can be beneficial, for example, in the case of rapid processes. By means of special optics, the fluorescence can be registered in a layer of only about 50 mm, but not in the entire well. This can be beneficial for background reduction in all measurements where the fluorescent dye is also present extracellularly. Such a situation can exist, for example, in the measurement of changes in membrane potential using DiBac dyes. Standard applications of the system are measurements of the intracellular calcium concentration or the membrane potential of cells. Among the dyes mentioned above, $DiBac_4(3)$, which, owing to its excitation maximum, is most suitable for the argon laser in the FLIPR, has the highest sensitivity for voltage differences.

Since the $DiBac_4(3)$ takes some time to come to equilibrium, the measurement can be taken after a certain incubation time. In embodiments, the incubation temperature is at or about the optimal temperature for growth and metabolism of the biological cells being used in the assay. For example, the incubation temperature can be at or about 37° C. Incubation time can be varied to achieve complete or uniform sample temperature. In embodiments, the sample can be incubated for at least about 10 minutes. In embodiments, the sample is incubated for about or precisely 30 minutes.

Although results can be obtained at any time desired, in order to obtain as reliable of a result as possible or practical, the results should be determined and, optionally, recorded as quickly as possible after each incubation step. This is because cooling of the dye solution might affect the result of the measurement. Thus, prior to any measurement, the composition to be measured can be incubated at a chosen temperature for a period of time that is sufficient to equilibrate the temperature of the composition at a desired level. For example, the composition can be incubated for at least about one minute, or at least about two, three, for, five, or even more minutes. Included are incubation periods prior to initial measurements (e.g., to determine base-line levels of activity or membrane potential). As with the other incubation periods, this pre-incubation phase can be carried out to compensate for temperature variations on the microtiter plate.

In embodiments where FLIPR is used, the measurement is typically carried out using the temperature parameters preset by the FLIPR manufacturer for the measurement of membrane potentials (about 37° C.). However, this is a guideline, and those practicing the invention can alter the temperature to achieve maximal results. Such temperature modifications are well within the skill of those in the art, and do not represent undue experimentation. In embodiments, the parameters preset by the FLIPR manufacturer are followed essentially precisely.

Although variations in volume can be accounted for, in the FLIPR, in embodiments of the present invention, the volume of the reaction solution in which the process is carried out is changed as little as possible. In embodiments where $DiBac_4(3)$ is used, the $DiBac_4(3)$ signal is most reproducible if only relatively small volume changes take place in the FLIPR; thus, the volume is typically maintained throughout, to the extent possible and practicable. Accordingly, in these embodiments, the substances to be tested are added as concentrated solutions. In embodiments, they are added at a concentration of at least about 2-fold. For example, they can be added in about a five-fold, ten-fold, or even greater concentrated form to the $DiBac_4(3)$-dyed cells.

Since the fluorescence measurement with the FLIPR Membrane Potential Assay Kit is not temperature-sensitive, it can be carried out simply at room temperature. This can be advantageous, for example, in embodiments that utilize the FLIPR II, which allows measurements with 384-well microtiter plates.

In embodiments, the HCN channels are activated by hyperpolarization (for example HCN2 at B100 mV to about 50%) and cause a depolarization of the cells. By increasing the intracellular cAMP concentration (for example with dibutyryl-cAMP or with forskolin), the value of the half-maximal activation can be shifted by about 10 mV to more positive potentials (Ludwig et al., 1998).

Electrophysiologically, HON channels can be studied easily on stably transfected cells using the patch-clamp method, as voltage changes can be brought about easily. In contrast, in the FLIPR, it is not possible to induce voltage changes, and exactly because of the HCN activity, a hyperpolarization of the cells would only be transient. It has not been possible to achieve hyperpolarization of the transfected cells by adding an HCN2 inhibitor (zatebradine), since the resting membrane potential of the transfected cells is much too far removed from the potentials at which HCN2 is activated.

On the one hand, hyperpolarization is required for HCN activation. However, on the other hand, under physiological conditions, an activated HCN leads immediately to depolarization. Accordingly, in the present invention, conditions are provided under which the HCN channels can be activated by hyperpolarization, but where depolarization by the activated HCN channel is initially impossible. To this end, the cells, for example cells seeded in microtiter plates, are washed in an isoosmolar buffer in which NaCl has been replaced by another chloride salt, such as choline chloride. In embodiments, the wash buffer also contains at least some KCl, since extracellular $K^+$ can improve HCN activation (Biel et al. 1999). In embodiments, the wash buffer contains at least 1 mM KCl. In embodiments, the wash buffer contains about 5 mM KCl. The wash buffer, which serves to effect hyperpolarization of the cation channels and thus the HCN cells, can also contain 5 $\mu$M $DiBac_4(3)$ for measuring changes in the membrane potential in the FLIPR. By removing the extracellular $Na^+$, the cells are hyperpolarized, i.e. the cation channel is activated. However, the HCN is not capable of causing depolarization of the cells, since the required concentration gradient of the ions $Na^+$ or $K^+$ transported by HCN is missing. Here, an activated HCN could only result in a more pronounced hyperpolarization. This is reflected in the fact that the initial fluorescence measured for HCN cells in the FLIPR at 10 $\mu$M forskolin is lower than that without forskolin, whereas there is no difference in nontransfected cells.

In the FLIPR, $Na^+$ is added to the cells, so that the activated HCN (after a few seconds, in which there are mixing effects) causes, from about 15 seconds after the addition of $Na^+$, depolarization of the cells, which becomes visible by an increase in fluorescence. The detection of HCN modulators can rely on a difference between cells having an activated HCN channel (e.g., only $Na^+$ addition) and cells having a blocked HCN channel (e.g., $Na^+$+8 mM CsCl). It has been determined that a greater difference provides a greater reliability in the system. For example, activation of the HCN channel by pre-incubation with 10 $\mu$M forskolin increases the difference between the uninhibited 100% value from the inhibited 0% value considerably.

One embodiment of the present invention relates to the comparative determination of the change in the membrane potential of at least two cell populations incubated with different concentrations of one of the substances to be examined. In this way, the optimal concentration of the substance(s) can be determined.

Substances that are to be examined for their activity are referred to as substances to be examined or substances to be tested. Substances that are active, i.e. that modulate the activity of the hyperpolarization-activated cation channel, can either be inhibitors (they inhibit the channel and reduce depolarization or prevent depolarization altogether) or be activators (they activate the channel and cause a more pronounced or more rapid depolarization) of the hyperpolarization-activated cation channel.

In embodiments, the invention provides a high-throughput screening (HTS) process. In HTS, the process can be used for identifying inhibitors and/or activators of a hyperpolarization-activated cation channel. Substances identified in this manner can be used, for example, as pharmaceutically active compounds. Thus, they can be used as medicaments (medicinal compositions) or as active ingredients of medicaments.

Accordingly, the invention also provides a process that comprises the formulation of an identified substance in a pharmaceutically acceptable form. In this aspect of the invention, the methods described above can be linked to formulation of an identified substance in a pharmaceutically acceptable form. Such forms, and processes for preparing such forms, are well known to, and widely practiced by, those of skill in the art. Therefore, they need not be detailed here. Examples include, but are not limited to, forms that comprise excipients or biologically tolerable carriers.

The invention also provides a process for preparing a medicament. The process comprises the identification of a substance that inhibits or activates the activity of a hyperpolarization-activated cation channel, and mixing the identified substance with a pharmaceutically acceptable excipient. In embodiments, the process for preparing a medicament comprises
a) the identification of a substance which modulates the activity of hyperpolarization-activated cation channels;
b) the preparation of the substance;
c) the purification of the substance; and
d) the mixing of the substance with a pharmaceutically acceptable excipient.

The invention also provides a kit. In embodiments, the kit is a test kit for determining whether a substance modulates the activity of a hyperpolarization-activated cation channel. In embodiments, the test kit comprises
a) cells that overexpress a hyperpolarization-activated cation channel;
b) an isoosmolar sodium-ion-free buffer for hyperpolarizing the cell; and
c) at least one reagent for detection of hyperpolarization activated cation channels.

The components/reagents can be those described in detail herein with respect to the assays of the invention. The components can be supplied in separate containers within the kit or in combinations within containers within the kit. Where applicable, components and/or reagents can be supplied in stabilized form. The stabilized form can permit the components and/or reagents to be maintained for extended periods of time without significant degradation or loss in activity. For example, the cells can be supplied in a cryogenic state. In addition, the salts (ions) or reagents that will comprise the assay composition can be provided in solid (dry) form, to be reconstituted with water or another appropriate solvent prior to use. Accordingly, the kit can comprise water.

As a measure for the activity of a substance, the change in the membrane potential of the cell is measured, for example, with the aid of a potential-sensitive fluorescent dye. As mentioned above, the dye can be an oxanol derivative, such as 3-bis-barbituric acid oxanol.

EXAMPLES

The invention will now be illustrated in more detail by various examples of embodiments of the invention. The following examples are exemplary only. Thus, the scope of the invention is not limited to the embodiments disclosed in the examples. Abbreviations used in the Examples are listed in Table 7 below.

Example 1

Preparation of Transfected Cells

The plasmid pcDNA3-muHCN2 contains the murine HCN2 (muHCN2) cDNA (Genbank Accession No. AJ225122) of Pos. 22–2812 (coding sequence: Pos. 36–2627), cloned into the EcoRI and NotI cleavage sites of pcDNA3, and was obtained from M. Biel, TU Munich (Ludwig et al., 1998). In each case 6 $\mu$g of this plasmid DNA were used for transfecting CHO or HEK293 cells. For transfecting CHO cells or HEK cells, the LipofectAmine™ Reagent from Life Technologies (Gaithersburg, Md., USA) was used, in accordance with the instructions of the manufacturer. 24 hours after the transfection, the cells were transferred from culture dishes into 75 cm$^2$ cell culture bottles. 72 hours after the transfection, the cells were subjected to a selection with 400 $\mu$g/ml of the antibiotic G418 (Calbiochem, Bad Soden, Germany). Following a two-week selection, the surviving cells were detached from the bottles using trypsin-EDTA, counted in the cell counter Coulter Counter Z1 and sown into 96-well microtiter plates such that statistically, 1 cell was present per well. The microtiter plates were checked regularly under the microscope, and only cells from wells in which only one colony was growing were cultured further.

From these cells, total RNA was isolated with the aid of the QlAshredder and RNeasy kits from Qiagen (Hilden, Germany). This total RNA was examined by RT-PCR for expression of muHCN2 (Primer 1): 5'-GCCAATACCAGGAGAAG-3' [SEQ ID NO. 7], corresponds to Pos. 1354–1370 and AJ225122, and primer 2:5'-TGAGTAGAGGCGACAGTAG-3' [SEQ ID NO. 8], corresponds to pos. 1829–1811 in AJ225122; expected RT-PCR band: 476 bp.

Example 2

Patch-Clamp Examination of the Cells

Using the patch-clamp method, the cells with detectable mRNA expression were examined electrophysiologically, in the whole-cell configuration, for functional expression of muHCN2. This method is described in detail in Hamill et al (1981), which is incorporated herein by reference. The cells were clamped to a holding potential of −40 mV. Starting with this holding potential, the ion channels were activated by a voltage change to B140 mV for a period of one second. The current amplitude was determined the end of this pulse. Among the transfected HEK cells, some were found having currents of about 1 nA; however, owing to interfering endogenous currents, it was not possible to construct an assay for these cells in the FLIPR.

However, in the HEK cells, it was found clearly that a functionally active HCN2 channel was only detectable in cells having strong mRNA expression. In the CHO cells, the correlation between mRNA expression and function was confirmed. In general, the mRNA expression in the HEK cells was about three times better than that in the CHO cells. In the patch-clamp studies, it was possible to demonstrate a weak current in some cells of one of the most strongly expressing CHO cell lines.

Example 3

Preparation of Doubly-Transfected Cells

Since the functional expression appeared to correlate strongly with the mRNA expression, we carried out a second transfection with the muHCN2 cDNA that had earlier been cloned into the EcoRI and NotI site of the vector pcDNA3.1 (+)zeo. After a two-week selection with G418 and Zeocin (Invitrogen, Groningen, NL), individual cell clones were isolated as described in Example 1. Following isolation of the total RNA from these cells, an RT-PCR with the primers mentioned in Example 1 was carried out. Then an RT-PCR was carried out with the following primers, comprising a region which contains the 3'-end of the coding sequence of muHAC1 (primer 3: 5'-AGTGGCCTCGACCCACTGGAC-TCT-3' [SEQ ID NO. 9], corresponds to pos. 2553–2576 in AJ225122, and primer 4: 5'-CCGCCTCCTAAGCTACCTA-CGTCCC-3' [SEQ ID NO. 10], corresponds to pos. 2725–2701 in AJ225122).

Some of the doubly-transfected cells showed a considerably more pronounced expression both in RT-PCR and in the patch-clamp analysis than the cells which had been transfected only once. Electrophysiologically, currents of up to 11 nA were measured. These cells were used for constructing an FLIPR assay for HCN2.

Example 4

Construction of an FLIPR Assay for HCN Channels

The cells seeded on the microtiter plates are washed in an isoosmolar buffer in which NaCl has been replaced by choline chloride. However, this wash buffer also contains 5 mM KCl, since extracellular $K^+$ is important for HCN activation (Biel et al. 1999). This wash buffer, which serves to effect hyperpolarization of the HCN cells, also contains 5 $\mu$M DiBac$_4$(3) for measuring changes in the membrane potential in the FLIPR. By removing the extracellular $Na^+$, the cells are hyperpolarized, i.e. the HCN is activated. However, the HCN is not capable of causing depolarization of the cells, since the required concentration gradient of the ions $Na^+$ or $K^+$ transported by HCN is missing. Here, an activated HCN could only result in a more pronounced hyperpolarization. This is reflected in the fact that the initial fluorescence measured for HCN cells in the FLIPR at 10 $\mu$M forskolin is lower than that without forskolin, whereas there is no difference in nontransfected cells.

Since DiBac$_4$(3) fluorescence may be sensitive to temperature variations, the measurement is, after an incubation at 37° C. for 30 minutes, carried out as quickly as possible—cooling of the dye solution may affect the measured results. Preferably, the sample is thermostated for five minutes in the FLIPR prior to the start of the measurement.

The substances to be tested are preferably added in 10-fold concentrated form to the cells which had been dyed with DiBac$_4$(3).

In the FLLPR, $Na^+$ is added to the cells so that the activated HCN (after a few seconds, in which there are mixing effects) causes, from about 15 seconds after the addition of $Na^+$, depolarization of the cells, which becomes visible by an increase in fluorescence. An activation of the HCN channel by preincubation with 10 $\mu$M forskolin increases the difference between the uninhibited 100% value from the inhibited 0% value considerably. By comparison with the control values, it can be detected whether a substance to be tested is an activator (more rapid or more pronounced depolarization) or an inhibitor (slower or inhibited depolarization).

Example 5

Determination of the IC50 of an HCN2 Blocker

Using the transfected HCN cells, the effect of various concentrations of the substance zatebradine, which is known as an $I_f$ blocker, were examined. The inhibition by zatebradine was calculated from the relative change in fluorescence from the time 60 seconds. For each concentration of the inhibitor, the mean of in each case 6 wells of the microtiter plate was determined. From these values, the IC50 of zatebradine was calculated as 26 $\mu$M, a value which corresponds well with the value of 31 $\mu$M determined electrophysiologically in the same cells.

Example 6

Use of the FLIPR Membrane Assay Kit (Molecular Devices, Sunnyvale, USA):

Cells that were seeded a day earlier are, as before, washed three times with in each case 400 $\mu$l of wash buffer per well. However, this time, the volume that remains above the cells after the last washing step is chosen depending on the desired $Na^+$ and $Cs^+$ concentrations. The dye, in wash buffer, is added, and the cells are incubated with dye for 30 minutes. The temperature is typically room temperature (about 21–25° C.), but can be about 37° C.

In the FLIPR, depolarization is then induced by addition of $Na^+$ and in some control wells inhibited again by simultaneous addition of $Cs^+$. Since, in the dye from Molecular Devices, an increase in the ionic strength might lead to changes in fluorescence, it has to be ensured that the ionic strength changes to the same degree in all wells of a microtiter plate. The desired final concentrations of sodium or cesium ions permitting, the osmolarity is not changed. To adjust the desired concentrations of $Na^+$ and $Cs^+$, two further buffers which, instead of 140 mM of choline chloride, contain 140 mM NaCl (sodium buffer) and 140 mM CsCl (cesium buffer), respectively, are used in addition to the wash buffer.

For measurements with the FLIPR Membrane Potential Assay Kit Molecular Devices gives the following standard protocol for 96-well microtiter plates (384 wells in brackets): On the day before the measurement, the cells are seeded in 100 ml (25 ml) of medium. Following addition of 100 $\mu$l (25 $\mu$l) of dye and 30 minutes of incubation at room temperature or at 37° C., 50 $\mu$l (25 $\mu$l) of the substance to be tested, in a suitable buffer, are added in the FLIPR.

Using the volumes stated by Molecular Devices, it is possible, without changing the ionic strength, to achieve a maximum concentration of 28 mM for $Na^++Cs^+$ in 96-well plates and a maximum concentration of 46.7 mM in 384-well plates. Since this concentration, in particular in the 96-well plates, is too low for optimum activity of the hyperpolarization-activated cation channels, different volumes are tested for the individual steps.

It has been found that the dye concentrations can be reduced to half of those in the protocol given by Molecular Devices.

In 96-well plates, good results are obtained even with the following volumes: 45 $\mu$l of wash buffer supernatant above the cells, 60 $\mu$l of dye in the wash buffer, 195 $\mu$l addition volume in the FLIPR. Such a high additional volume allows a maximum concentration of $Na^++Cs^+$ of 91 mM, i.e. at 8–10 mM CsCl, the final NaCl concentration can be 81–83 mM. For 80 mM $Na^+$ and 8 mM $Cs^+$, 6.43 $\mu$l of wash buffer, 171.43 $\mu$l of sodium buffer and 17.14 $\mu$l of cesium buffer are required, based on an added volume of 195 $\mu$l.

Materials and Methods

The following materials and methods were, and can be, used to practice the invention as described in the Examples above. Other materials and methods can be used to practice other embodiments of the invention. Thus, the invention is not limited to the materials and methods disclosed below.

1. Solutions and buffers for the measurement with $DiBac_4(3)$

A: $DiBac_4(3)$ bis-(1,3-dibutylbarbituric acid)trimethine oxonol From Molecular Probes, Cat. No. B-438, MW: 516.64 g/mol A 10 mM stock solution of $DiBac_4(3)$ is made up in DMSO (25 mg of $DiBac_4(3)$/4.838 ml of DMSO). Aliquots of this stock solution are stored at −20° C. Final concentration during dyeing and addition: 5 µM.

B: Forskolin MW: 410.5 g/mol Final concentration during dyeing: 10 µM Aliquots of a 10 mM stock solution in DMSO are stored at −20° C.

C: Wash buffer: (140 mM choline chloride, 5 mM KCl, 1 mM $CaCl_2$, 1 mM $MgCl_2$, 10 mM HEPES, 5 mM glucose, adjusted to pH 7.4 with 1 M KOH)

D: Presoak solution for saturating the tips of the pipettes: as wash buffer+10 µM $DiBac_4(3)$ This solution is only used for the presoak plate.

E: Dye solution: double concentrated, i.e. wash buffer+10 µM $DiBac_4(3)$+20 µM forskolin F: 10-fold concentrated solution for the addition plate: 500 mM NaCl in $H_2O$+5 µM $DiBac_4(3)$ All substances are made up in this solution in 10-fold concentrated form. Positive control (final concentration): 50 mM NaCl Negative control (final concentration): 50 mM NaCl+8 mM CsCl 2. Solutions and buffers for the measurements with the FLIPR Membrane Potential Assay Kit from Molecular Devices A: FLIPR Membrane Potential Assay Kit, from Molecular Probes, Cat. No. R8034

B: Wash buffer: (140 mM choline chloride, 5 mM KCl, 1 mM $CaCl_2$, 1 mM $MgCl_2$, 10 mM HEPES, 5 mM glucose, adjusted to pH 7.4 with 1M KOH).

C: Dye buffer: (content of one of the "reagent vials" of the FLIPR Membrane Potential Assay Kit in 10 ml of wash buffer)

D: Sodium buffer: (140 mM NaCl, 5 mM KCl, 1 mM $CaCl_2$, 1 mM $MgCl_2$, 10 mM HEPES, 5 mM glucose, adjusted to pH 7.4 with 1M KOH).

E: Cesium buffer: (140 mM CsCl, 5 mM KCl, 1 mM $CaCl_2$, 1 mM $MgCl_2$, 10 mM HEPES, 5 mM glucose, adjusted to pH 7.4 with 1M KOH).

3. Cell culture operations:

The day before the measurement, the muHCN2-transfected CHO cells are seeded at a density of 35 000 cells/well, in each case in 200 µl of complete medium, into black 96-well microtiter plates. The cells are incubated at 37° C. and 5% $CO_2$ overnight.

4. Dyeing with $DiBac_4(3)$ and measurement in FLIPR:

Before dyeing, the cells are washed three times with 400 µl of wash buffer in a cell washer. After the last washing step, a residual volume of 90 µl of wash buffer/well remains above the cells.

The washed cells (with 90 µl of wash buffer/well) are in each case incubated with 90 µl of dye solution/well at 37° C. in the $CO_2$ incubator for 30 minutes. After this incubation time, the cell plate is measured in the FLIPR at about 37° C. (preset temperature setting of the FLIPR manufacturer for measurement of membrane potentials with $DiBac_4(3)$), either immediately or after five minutes of thermostating.

The snapshot (initial fluorescence before the start of the measurement) should on average be about 35 000 units. In the maximum, the FLIPR can resolve up to about 65 000 units.

When the program is started, the tips of the pipettes are initially saturated by immersion into presoak solution with $DiBac_4(3)$. Following this step, the actual measurement is initiated with the first measurement (t=0 seconds). Since $DiBac_4(3)$ is a slow-response dye, it is sufficient to determine the fluorescence in the wells of the microtiter plate every 5 seconds. After about 20 seconds, the substances, which are present in the addition plate in 10-fold concentrated form, are added simultaneously to the microtiter plate using the pipettor. Since the volume after dyeing is 180 µl, 20 µl are added to each well. The measurement of the fluorescence can be terminated after about 5 minutes. For evaluation, the change in fluorescence in the interval where it is linear and in which uninhibited HCN2-transfected cells differ significantly from inhibited cells is examined.

5. Dyeing with the FLIPR Membrane Potential Assay Kit and measurement in the FLIPR.

Before dyeing, the cells are washed three times with 400 µl of wash buffer in a cell washer. After the last washing step, a residual volume of 45–90 µl of wash buffer/well remains above the cells.

Following addition of the dye solution (the volume depends on the desired final concentrations), the samples are incubated at room temperature (preferred) or at 37° C. in a $CO_2$ incubator for 30 minutes. Following this incubation time, the cell plate is measured at room temperature in the FLIPR.

In the FLIPR Membrane Potential Assay Kit the snapshot (initial fluorescence before the start of the measurement) may be lower than that during the measurement with $DiBac_4(3)$, since the assay kit is more sensitive to changes in the membrane potential than $DiBac_4(3)$.

Owing to the higher achievable sensitivity, the measurement should, wherever possible (FLIPRII), be carried out using an emission filter which is transparent to light above 550 nm. However, it is also possible to carry out the measurements using the standard filter, which is transparent between 510 and 580 nm.

When the program is started (t=0), the FLIPR initially determines the fluorescence of all wells of the plate a number of times, before the depolarization is started after about 20 seconds by addition of sodium ions. In each case, the addition solution is mixed from the three buffers (wash buffer, sodium buffer and cesium buffer) such that the addition results in no change of the osmolarity, or in a change which is identical in all wells. The measurement of the fluorescence can be terminated after about 5 minutes. The wells to which, in addition to $Na^+$, 8 mM $Cs^+$ were added to block the HCN channel completely serve as negative control. By deducting these values from the others, a good measure for the activity of the HCN channel under the influence of the substance to be examined is obtained. For evaluation, the change in fluorescence in the interval where it is linear and in which uninhibited HCN2-transfected cells differ significantly from inhibited cells is examined.

REFERENCES

All references disclosed herein, including the following references, are hereby incorporated herein by reference.

Biel M., Ludwig A., Zong X., Hofmann R. (1999) Hyperpolarization-activated cation channels: A multigene family. Rev. Physiol. Biochem. Pharmacol. 136: 165–181.

Hamill O. P., Marty A., Neher E., Sakmann B., Sigworth F. J. (1981) Improved patch-clamp techniques for high-resolution current recording from cells and cell-free membrane patches. Pflügers Arch. 391: 85–100.

Ludwig A., Zong X., Jeglitsch M., Hofmann F., Biel M. (1998) A family of hyperpolarization-activated mammalian cation channels. Nature 393: 587–591.

Ludwig A., Zong X., Stieber J., Hullin R., Hofmann R., Biel M. (1999) Two pacemaker channels from heart with profoundly different activation kinetics. EMBO J. 18: 2323–2329.

Reiffen A., Eberlein W., Müller P., Psiorz M., Noll K., Heider J., Lillie C., Kobinger W., Luger P. (1990) Specific bradycardiac agents. 1. Chemistry, pharmacology, and structure-activity relationships of substituted benzazepinones, a new class of compounds exerting anti-ischemic properties. J. Med. Chem. 33: 1496–1504.

TABLE 1

SEQ ID NO.1 Protein sequence of huHCN2

Accession number: AAC28444

```
  1 MDARGGGGRP GESPGASPTT GPPPPPPPRP PKQQPPPPPP PAPPPGPGPA PPQHPPRAEA
 61 LPPEAADEGG PRGRLRSRDS SCGRPGTPGA ASTAKGSPNG ECGRGEPQCS PAGFEGPARG
121 PKVSFSCRGA ASGPAPGPGP AEEAGSEEAG PAGEPRGSQA SFMQRQFGAL LQPGVNKFSL
181 RMFGSQKAVE REQERVKSAG AWIIHPYSDF RFYWDFTMLL FMVGNLIIIP VGITFFKDET
241 TAPWIVFNVV SDTFFLMDLV LNFRTGIVIE DNTEIILDPE KIKKKYLRTW FVVDFVSSIP
301 VDYIFLIVEK GIDSEVYKTA RALRIVRFTK ILSLLRLLRL SRLIRYIHQW EEIFRMTYDL
361 ASAVMRICNL ISMMLLLCHW DGCLQFLVPM LQDFPRNCWV SINGMVNRSW SELYSFALFK
421 AMSHMLCIGY GRQAPESMTD IWLTMLSMIV GATCYAMFIG HATALIQSLD SSRRQYQEKY
481 KQVEQYMSFH KLPADFRQKI HDYYEHRYQG KMFDEDSILG ELNGPLREEI VNFNCRKLVA
541 SMPLFANADP NFVTAMLTKL KFEVFQPGDY IIREGTIGKK MYFIQHGVVS VLTKGNKEMK
601 LSDGSYFGEI CLLTRGRRTA SVRADTYCRL YSLSVDNFNE VLEEYPMMRR AFETVAIDRL
661 DRIGKKNSIL LHKVQHDLNS GVFNNQENAI IQEIVKYDRE MVQQAELGQR VGLFPPPPPP
721 PQVTSAIATL QQAAAMSFCP QVARPLVGPL ALGSPRLVRR PPPGPAPAAA SPGPPPPASP
781 PGAPASPRAP RTSPYGGLPA APLAGPALPA RRLSRASRPL SASQPSLPHG APGPAASTRP
841 ASSSTPRLGP TPAARAAAPS PDRRDSASPG AAGGLDPQDS ARSRLSSNL
```

TABLE 2

SEQ ID NO.2 Nucleotide sequence of huHCN2

Accession number: AF065164

```
  1 CGGCTCCGCT CCGCACTGCC CGGCGCCGCC TCGCCATGGA CGCGCGCGGG GGCGGCGGGC
 61 GGCCCGGGGA GAGCCCGGGC GCGAGCCCCA CGACCGGGCC GCCGCCGCCG CCGCCCCCGC
121 GCCCCCCCAA ACAGCAGCCG CCGCCGCCGC CGCCGCCCGC GCCCCCCCCG GGCCCCGGGC
181 CCGCGCCCCC CCAGCACCCG CCCCGGGCCG AGGCGTTGCC CCCGGAGGCG GCGGATGAGG
241 GCGGCCCGCG GGGCCGGCTC CGCAGCCGCG ACAGCTCGTG CGGCCGCCCC GGCACCCCGG
301 GCGCGGCGAG CACGGCCAAG GCAGCCCGA ACGGCGAGTG CGGGCGCGGC GAGCCGCAGT
361 GCAGCCCCGC GGGGCCCGAG GGCCCGGCGC GGGGGCCCAA GGTGTCGTTC TCGTGCCGCG
421 GGGCGGCCTC GGGGCCCGCG CCGGGGCCGG GGCCGGCGGA GGAGGCGCGC AGCGAGGAGG
481 CGGGCCCGGC GGGGGAGCCG CGCGGCAGCC AGGCCAGCTT CATGCAGCGC CAGTTCGGCG
541 CGCTCCTGCA GCCGGGCGTC AACAAGTTCT CGCTGCGGAT GTTCGGCAGC CAGAAGGCCG
601 TGGAGCGCGA GCAGGAGCGC GTCAAGTCGG CGGGGGCCTG GATCATCCAC CCGTACAGCG
661 ACTTCAGGTT CTACTGGGAC TTCACCATGC TGCTGTTCAT GGTGGGAAAC CTCATCATCA
721 TCCCAGTGGG CATCACCTTC TTCAAGGATG AGACCACTGC CCCGTGGATC GTGTTCAACG
781 TGGTCTCGGA CACCTTCTTC CTCATGGACC TGGTGTTGAA CTTCCGCACC GGCATTGTGA
```

TABLE 2-continued

SEQ ID NO.2 Nucleotide sequence of huHCN2

Accession number: AF065164

```
 841 TCGAGGACAA CACGGAGATC ATCCTGGACC CCGAGAAGAT CAAGAAGAAG TATCTGCGCA
 901 CGTGGTTCGT GGTGGACTTC GTGTCCTCCA TCCCCGTGGA CTACATCTTC CTTATCGTGG
 961 AGAAGGGCAT TGACTCCGAG GTCTACAAGA CGGCACGCGC CCTGCGCATC GTGCGCTTCA
1021 CCAAGATCCT CAGCCTCCTG CGGCTGCTGC GCCTCTCACG CCTGATCCGC TACATCCATC
1081 AGTGGGAGGA GATCTTCCAC ATGACCTATG ACCTGGCCAG CGCGGTGATG AGGATCTGCA
1141 ATCTCATCAG CATGATGCTG CTGCTCTGCC ACTGGGACGG CTGCCTGCAG TTCCTGGTGC
1201 CTATGCTGCA GGACTTCCCG CGCAACTGCT GGGTGTCCAT CAATGGCATG GTGAACCACT
1261 CGTGGAGTGA ACTGTACTCC TTCGCACTCT TCAAGGCCAT GAGCCACATG CTGTGCATCG
1321 GGTACGGCCG GCAGGCGCCC GAGAGCATGA CGGACATCTG GCTGACCATG CTCAGCATGA
1381 TTGTGGGTGC CACCTGCTAC GCCATGTTCA TCGGCCACGC CACTGCCCTC ATCCAGTCGC
1441 TGGACTCCTC GCGGCGCCAG TACCAGGAGA AGTACAAGCA GGTGGAGCAG TACATGTCCT
1501 TCCACAAGCT GCCAGCTGAC TTCCGCCAGA AGATCCACGA CTACTATGAG CACCGTTACC
1561 AGGGCAAGAT GTTTGACGAG GACAGCATCC TGGGCGAGCT CAACGGGCCC CTGCGGGAGG
1621 AGATCGTCAA CTTCAACTGC CGGAAGCTGG TGGCCTCCAT GCCGCTGTTC GCCAACGCCG
1681 ACCCCAACTT CGTCACGGCC ATGCTGACCA AGCTCAAGTT CGAGGTCTTC CAGCCGGGTG
1741 ACTACATCAT CCGCGAAGGC ACCATCGGGA AGAAGATGTA CTTCATCCAG CACGGCGTGG
1801 TCAGCGTGCT CACTAAGGGC AACAAGGAGA TGAAGCTGTC CGATGGCTCC TACTTCGGGG
1861 AGATCTGCCT GCTCACCCGG GGCCGCCGCA CGGCGAGCGT GCGGGCTGAC ACCTACTGCC
1921 GCCTCTATTC GCTGAGCGTG GACAACTTCA ACGAGGTGCT GGAGGAGTAC CCCATGATGC
1981 GGCGCGCCTT CGAGACGGTG GCCATCGACC GCCTGGACCG CATCGGCAAG AAGAATTCCA
2041 TCCTCCTGCA CAAGGTGCAG CATGACCTCA ACTCGGGCGT ATTCAACAAC CAGGAGAACG
2101 CCATCATCCA GGAGATCGTC AAGTACGACC GCGAGATGGT GCAGCAGGCC GAGCTGGGTC
2161 AGCGCGTGGG CCTCTTCCCG CCGCCGCCGC CGCCGCCGCA GGTCACCTCG GCCATCGCCA
2221 CGCTGCAGCA GGCGGCGGCC ATGAGCTTCT GCCCGCAGGT GGCGCGGCCG CTCGTGGGGC
2281 CGCTGGCGCT CGGCTCGCCG CGCCTCGTGC GCCGCCCGCC CCCGGGGCCC GCACCTGCCG
2341 CCGCCTCACC CGGGCCCCCG CCCCCCGCCA GCCCCCGGG CGCGCCCGCC AGCCCCGGG
2401 CACCGCGGAC CTCGCCCTAC GGCGGCCTGC CGCCGCCCC CCTTGCTGGG CCCGCCCTGC
2461 CCGCGCGCCG CCTGAGCCGC GCGTCGCGCC CACTGTCCGC CTCGCAGCCC TCGCTGCCTC
2521 ACGGCGCCCC CGGCCCCGCG GCCTCCACAC GCCCGGCCAG CAGCTCCACA CCGCGCTTGG
2581 GGCCCACGCC CGCTGCCCGG GCCGCCGCGC CCAGCCCGGA CCGCAGGGAC TCGGCCTCAC
2641 CCGGCGCCGC CGGCGGCCTG GACCCCCAGG ACTCCGCGCG CTCGCGCCTC TCGTCCAACT
2701 TGTGACCCTC GCCGACCGCC CCGCGGGCCC AGGCGGGCCG GGGCGGGGC CGTCATCCAG
2761 ACCAAAGCCA TGCCATTGCG CTGCCCCGGC CGCCAGTCCG CCCAGAAGCC ATAGACGAGA
2821 CGTAGGTAGC CGTAGTTGGA CGGACGGGCA GGGCCGGCGG GGCAGCCCCC TCCGCGCCCC
2881 CGGCCGTCCC CCCTCATCGC CCCGCGCCCA CCCCCATCGC CCCTGCCCCC GGCGGCGGCC
2941 TCGCGTGCGA GGGGGCTCCC TTCACCTCGG TGCCTCAGTT CCCCCAGCTC TAAGACAGGG
3001 ACGGGGCGGC CCAGTGGCTG AGAGGAGCCG GCTGTGGAGC CCCGCCCGCC CCCCACCCTC
```

TABLE 2-continued

SEQ ID NO.2 Nucleotide sequence of huHCN2

Accession number: AF065164

```
3061 TAGGTGGCCC CCGTCCGAGG AGGATCGTTT TCTAAGTGCA ATACTTGGCC CGCCGGCTTC

3121 CCGCTGCCCC CATCGCGCTC ACGCAATAAC CGGCCCGGCC CCCGTCCGCG CGCGTCCCCC

3181 GGTGACCTCG GGGAGCAGCA CCCCGCCTCC CTCCAGCACT GGCACCGAGA GGCAGGCCTG

3241 GCTGCGCAGG GCGCGGGGGG GAGGCTGGGG TCCCGCCGCC GTGATGAATG TACTGACGAG

3301 CCGAGGCAGC AGTGCCCCCA CCGTGGCCCC CCACGCCCCA TTAACCCCCA CACCCCCATT

3361 CCGCGCAATA AA
```

TABLE 3

SEQ ID NO.3 Protein sequence of huHCN4

Accession number: HSA132429

```
   1 MDKLPPSMRK RLYSLPQQVG AKAWIMDEEE DAEEEGAGGR QDPSRRSIRL

51 RPLPSPSPSA AAGGTESRSS ALGAADSEGP ARGAGKSSTN GDCRRFRGSL

101 ASLGSRGGGS GGTGSGSSHG HLHDSAEERR LIAEGDASPG EDRTPPGLAA

151 EPERPGASAQ PAASPPPPQQ PPQPASASCE QPSVDTAIKV EGGAAAGDQI

201 LPEAEVRLGQ AGFMQRQFGA MLQPGVNKFS LRMFGSQKAV EREQERVKSA

251 GFWIIHPYSD FRFYWDLTML LLMVGNLIII PVGITFFKDE NTTPWIVFNV

301 VSDTFFLIDL VLNFRTGIVV EDNTEIILDP QRIKMKYLKS WFMVDFISSI

351 PVDYIFLIVE TRIDSEVYKT ARALRIVRFT KILSLLRLLR LSRLIRYIHQ

401 WEEIFHMTYD LASAVVRIVN LIGMMLLLCH WDGCLQFLVP MLQDFPDDCW

451 VSINNMVNNS WGKQYSYALF KAMSHMLCIG YGRQAPVGMS DVWLTMLSMI

501 VGATCYAMFI GHATALIQSL DSSRRQYQEK YKQVEQYMSF HKLPPDTRQR

551 IHDYYEHRYQ GKMFDEESIL GELSEPLREE IINFNCRKLV ASMPLFANAD

601 PNFVTSMLTK LRFEVFQPGD YIIREGTIGK KMYFIQHGVV SVLTKGNKET

651 KLADGSYFGE ICLLTRGRRT ASVRADTYCR LYSLSVDNFN EVLEEYPMMR

701 RAFETVALDR LDRIGKKNSI LLHKVQHDLN SGVFNYQENE IIQQIVQHDR

751 EMAHCAHRVQ AAASATPTPT PVIWTPLIQA PLQAAAATTS VAIALTHHPR

801 LPAAIFRPPP GSGLGNLGAG QTPRHLKRLQ SLIPSALGSA SPASSPSQVD

851 TPSSSSFHIQ QLAGFSAPAG LSPLLPSSSS SPPPGACGSP SAPTPSAGVA

901 ATTIAGFGHF HKALGGSLSS SDSPLLTPLQ PGARSPQAAQ PSPAPPGARG

951 GLGLPEHFLP PPPSSRSPSS SPGQLGQPPG ELSLGLATGP LSTPETPPRQ

1001 PEPPSLVAGA SGGASPVGFT PRGGLSPPGH SPGPPRTFPS APPRASGSHG

1051 SLLLPPASSP PPPQVPQRRG TPPLTPGRLT QDLKLISASQ PALPQDGAQT

1101 LRRASPHSSG ESMAAFPLFP RAGGGSGGSG SSGGLGPPGR PYGAIPGQHV

1151 TLPRKTSSGS LPPPLSLFGA RATSSGGPPL TAGPQREPGA RPEPVRSKLP

1201 SNL*
```

TABLE 4

SEQ ID NO.4 Nucleotide sequence of huHCN4

Accession number: HSA132429

```
   1 GGTCGCTGGG CTCCGCTCGG TTGCGGCGGG AGCCCCGGGA CGGGCCGGAC GGGCCGGGGC
  61 AGAGGAGGCG AGGCGAGCTC GCGGGTGGCC AGCCACAAAG CCCGGGCGGC GAGACAGACG
 121 GACAGCCAGC CCTCCCGCGG GACGCACGCC CGGGACCCGC GCGGGCCGTG CGCTCTGCAC
 181 TCCGGAGCGG TTCCCTGAGC GCCGCGGCCG CAGAGCCTCT CCGGCCGGCG CCCATTGTTC
 241 CCCGCGGGGG CGGGGCGCCT GGAGCCGGGC GGCGCGCCGC GCCCCTGAAC GCCAGAGGGA
 301 GGGAGGGAGG CAAGAAGGGA GCGCGGGGTC CCCGCGCCCA GCCGGGCCCG GGAGGAGGTG
 361 TAGCGCGGCG AGCCCGGGGA CTCGGAGCGG GACTAGGATC CTCCCCGCGG CGCGCAGCCT
 421 GCCCAAGCAT GGGCGCCTGA GGCTGCCCCC ACGCCGGCGG CAAAGGACGC GTCCCCACGG
 481 GCGGACTGAC CGGCGGGCGG ACCTGGAGCC CGTCCGCGGC GCCGCGCTCC TGCCCCCGGC
 541 CCGGTCCGAC CCCGGCCCCT GGCGCCATGG ACAAGCTGCC GCCGTCCATG CGCAAGCGGC
 601 TCTACAGCCT CCCGCAGCAG GTGGGGGCCA AGGCGTGGAT CATGGACGAG AAGAGGACG
 661 CCGAGGAGGA GGGGGCCGGG GGCCGCCAAG ACCCCAGCCG CAGGAGCATC CGGCTGCGGC
 721 CACTGCCCTC GCCCTCCCCC TCGGCGGCCG CGGGTGGCAC GGAGTCCCGG AGCTCGGCCC
 781 TCGGGGCAGC GGACAGCGAA GGGCCGGCCC GCGGCGCGGG CAAGTCCAGC ACGAACGGCG
 841 ACTGCAGGCG CTTCCGCGGG AGCCTGGCCT CGCTGGGCAG CCGGGCGGC GGCAGCGGCG
 901 GCACGGGGAG CGGCAGCAGT CACGGACACC TGCATGACTC CGCGGAGGAG CGGCGGCTCA
 961 TCGCCGAGGG CGACGCGTCC CCCGGCGAGG ACAGGACGCC CCCAGGCCTG GCGGCCGAGC
1021 CCGAGCGCCC CGGCGCCTCG GCGCAGCCCG CAGCCTCGCC GCCGCCGCCC CAGCAGCCAC
1081 CGCAGCCGGC CTCCGCCTCC TGCGAGCAGC CCTCGGTGGA CACCGCTATC AAAGTGGAGG
1141 GAGGCGCGGC TGCCGGCGAC CAGATCCTCC CGGAGGCCGA GGTGCGCCTG GCCAGGCCG
1201 GCTTCATGCA GCGCCAGTTC GGGGCCATGC TCCAACCCGG GGTCAACAAA TTCTCCCTAA
1261 GGATGTTCGG CAGCCAGAAA GCCGTGGAGC GCGAACAGGA GAGGGTCAAG TCGGCCGGAT
1321 TTTGGATTAT CCACCCCTAC AGTGACTTCA GATTTTACTG GGACCTGACC ATGCTGCTGC
1381 TGATGGTGGG AAACCTGATT ATCATTCCTG TGGGCATCAC CTTCTTCAAG GATGAGAACA
1441 CCACACCCTG GATTGTCTTC AATGTGGTGT CAGACACATT CTTCCTCATC GACTTGGTCC
1501 TCAACTTCCG CACAGGGATC GTGGTGGAGG ACAACACAGA GATCATCCTG GACCCGCAGC
1561 GGATTAAAAT GAAGTACCTG AAAAGCTGGT TCATGGTAGA TTTCATTTCC TCCATCCCCG
1621 TGGACTACAT CTTCCTCATT GTGGAGACAC GCATCGACTC GGAGGTCTAC AAGACTGCCC
1681 GGGCCCTGCG CATTGTCCGC TTCACGAAGA TCCTCAGCCT CTTACGCCTG TTACGCCTCT
1741 CCCGCCTCAT TCGATATATT CACCAGTGGG AAGAGATCTT CCACATGACC TACGACCTGG
1801 CCAGCGCCGT GGTGCGCATC GTGAACCTCA TCGGCATGAT GCTCCTGCTC TGCCACTGGG
1861 ACGGCTGCCT GCAGTTCCTG GTACCCATGC TACAGGACTT CCCTGACGAC TGCTGGGTGT
1921 CCATCAACAA CATGGTGAAC AACTCCTGGG GGAAGCAGTA CTCCTACGCG CTCTTCAAGG
1981 CCATGAGCCA CATGCTGTGC ATCGGCTACG GCGGCAGGC GCCCGTGGGC ATGTCCGACG
2041 TCTGGCTCAC CATGCTCAGC ATGATCGTGG GTGCCACCTG CTACGCCATG TTCATTGGCC
2101 ACGCCACTGC CCTCATCCAG TCCCTGGACT CCTCCCGGCG CCAGTACCAG CAAAAGTACA
2161 AGCAGGTGGA GCAGTACATG TCCTTTCACA AGCTCCCGCC CGACACCCGG CAGCGCATCC
2221 ACGACTACTA CGAGCACCGC TACCAGGGCA AGATGTTCGA CGAGGAGAGC ATCCTGGGCG
```

TABLE 4-continued

SEQ ID NO.4 Nucleotide sequence of huHCN4

Accession number: HSA132429

```
2281 AGCTAAGCGA GCCCCTGCGG GAGGAGATCA TCAACTTTAA CTGTCGGAAG CTGGTGGCCT
2341 CCATGCCACT GTTTGCCAAT GCGGACCCCA ACTTCGTGAC GTCCATGCTG ACCAAGCTGC
2401 GTTTCGAGGT CTTCCAGCCT GGGGACTACA TCATCCGGGA AGGCACCATT GGCAAGAAGA
2461 TGTACTTCAT CCAGCATGGC GTGGTCAGCG TGCTCACCAA GGGCAACAAG GAGACCAAGC
2521 TGGCCGACGG CTCCTACTTT GGAGAGATCT GCCTGCTGAC CCGGGGCCGG CGCACAGCCA
2581 GCGTGAGGGC CGACACCTAC TGCCGCCTCT ACTCGCTGAG CGTGGACAAC TTCAATGAGG
2641 TGCTGGAGGA GTACCCCATG ATGCGAAGGG CCTTCGAGAC CGTGGCGCTG GACCGCCTGG
2701 ACCGCATTGG CAAGAAGAAC TCCATCCTCC TCCACAAAGT CCAGCACGAC CTCAACTCCG
2761 GCGTCTTCAA CTACCAGGAG AATGAGATCA TCCAGCAGAT TGTGCAGCAT GACCGGGAGA
2821 TGGCCCACTG CGCGCACCGC GTCCAGGCTG CTGCCTCTGC CACCCCAACC CCCACGCCCG
2881 TCATCTGGAC CCCGCTGATC CAGGCACCAC TGCAGGCTGC CGCTGCCACC ACTTCTGTGG
2941 CCATAGCCCT CACCCACCAC CCTCGCCTGC CTGCTGCCAT CTTCCGCCCT CCCCCAGGAT
3001 CTGGGCTGGG CAACCTCGGT GCCGGGCAGA CGCCAAGGCA CCTGAAACGG CTGCAGTCCC
3061 TGATCCCTTC TGCGCTGGGC TCCGCCTCGC CCGCCAGCAG CCCGTCCCAG GTGGACACAC
3121 CGTCTTCATC CTCCTTCCAC ATCCAACAGC TGGCTGGATT CTCTGCCCCC GCTGGACTGA
3181 GCCCACTCCT GCCCTCATCC AGCTCCTCCC CACCCCCCGG GGCCTGTGGC TCCCCCTCGG
3241 CTCCCACACC ATCAGCTGGC GTAGCCGCCA CCACCATAGC CGGGTTTGGC CACTTCCACA
3301 AGGCGCTGGG TGGCTCCCTG TCCTCCTCCG ACTCTCCCCT GCTCACCCCG CTGCAGCCAG
3361 GCGCCCGCTC CCCGCAGGCT GCCCAGCCAT CTCCCGCGCC ACCCGGGGCC CGGGGAGGCC
3421 TGGGACTCCC GGAGCACTTC CTGCCACCCC CACCCTCATC CAGATCCCCG TCATCTAGCC
3481 CCGGGCAGCT GGGCCAGCCT CCCGGGGAGT TGTCCCTAGG TCTGGCCACT GGCCCACTGA
3541 GCACGCCAGA GACACCCCCA CGGCAGCCTG AGCCGCCGTC CCTTGTGGCA GGGGCCTCTG
3601 GGGGGGCTTC CCCTGTAGGC TTTACTCCCC GAGGAGGTCT CAGCCCCCCT GGCCACAGCC
3661 CAGGCCCCCC AAGAACCTTC CCGAGTGCCC CGCCCCGGGC CTCTGGCTCC CACGGATCCT
3721 TGCTCCTGCC ACCTGCATCC AGCCCCCCAC CACCCCAGGT CCCCCAGCGC CGGGGCACAC
3781 CCCCGCTCAC CCCCGGCCGC CTCACCCAGG ACCTCAAGCT CATCTCCGCG TCTCAGCCAG
3841 CCCTGCCTCA GGACGGGGCG CAGACTCTCC GCAGAGCCTC CCCGCACTCC TCAGGGGAGT
3901 CCATGGCTGC CTTCCCGCTC TTCCCCAGGG CTGGGGGTGG CAGCGGGGGC AGTGGGAGCA
3961 GCGGGGGCCT CGGTCCCCCT GGGAGGCCCT ATGGTGCCAT CCCCGGCCAG CACGTCACTC
4021 TGCCTCGGAA GACATCCTCA GGTTCTTTGC CACCCCCTCT GTCTTTGTTT GGGGCAAGAG
4081 CCACCTCTTC TGGGGGGCCC CCTCTGACTG CTGGACCCCA GAGGGAACCT GGGGCCAGGC
4141 CTGAGCCAGT GCGCTCCAAA CTGCCATCCA ATCTATGAGC TGGGCCCTTC CTTCCCTCTT
4201 CTTTCTTCTT TTCTCTCCCT TCCTTCTTCC TTCAGGTTTA ACTGTGATTA GGAGATATAC
4261 CAATAACAGT AATAATTATT TAAAAAACCA CACACACCAG AAAAACAAAA GACAGCAGAA
4321 AATAACCAGG TATTCTTAGA GCTATAGATT TTTGGTCACT TGCTTTTATA GACTATTTTA
4381 ATACTCAGCA CTAGAGGGAG GGAGGGGGAG GGAGGAGGGA GCAGGCAGGT CCCAAATGCA
4441 AAAGCCAGAG AAAGGCAGAT GGGGTCTCCG GGGCTGGGCA GGGGTGGGAG TGGCCAGTGT
```

TABLE 4-continued

SEQ ID NO.4 Nucleotide sequence of huHCN4

Accession number: HSA132429

```
4501 TGGCGGTTCT TAGAGCAGAT GTGTCATTGT GTTCATTTAG AGAAACAGCT GCCATCAGCC
4561 CGTTAGCTGT AACTTGGAGC TCCACTCTGC CCCCAGAAAG GGGCTGCCCT GGGGTGTGCC
4621 CTGGGGAGCC TCAGAAGCCT GCGACCTTGG GAGAAAAGGG CCAGGGCCCT GAGGGCCTAG
4681 CATTTTTTCT ACTGTAAACG TAGCAAGATC TGTATATGAA TATGTATATG TATATGTATG
4741 TAAGATGTGT ATATGTATAG CTATGTAGCG CTCTGTAGAG CCATGTAGAT AGCCACTCAC
4801 ATGTGCGCAC ACGTGTGCGG TCTAGTTTAA TCCCATGTTG ACAGGATGCC CAGGTCACCT
4861 TACACCCAGC AACCCGCCTT GGCCCGCAGG CTGTGCACTG CATGGTCTAG GGACGTTCTC
4921 TCTCCAGTCC TCAGGGAAGA GGACGCCAGG ACTTCGCAGC AGGCCCCCTC TCTCCCCATC
4981 TCTGGTCTCA AAGCCAGTCC CAGCCTGACC TCTCACCACA CGGAAGTGGA AGACTCCCCT
5041 TTCCTAGGGC CTCAAGCACA CACCG
```

TABLE 5

SEQ ID NO.5 Protein sequence of muHCN2

Accession number: CAA12406

```
  1 MDARGGGRP GDSPGTTPAP GPPPPPPPPA PPQPQPPPAP PPNPTTPSHP ESADEPGPRA
 61 RLCSRDSACT PGAAKGGANG ECGRGEPQCS PEGPARGPKV SFSCRGAASG PSAAEEAGSE
121 EAGPAGEPRG SQASFLQRQF GALLQPGVNK FSLRMFGSQK AVEREQERVK SAGAWIIHPY
181 SDFRFYWDFT MLLFMVGNLI IIPVGITFFK DETTAPWIVF NVVSDTFFLM DLVLNFRTGI
241 VIEDNTEIIL DPEKIKKKYL RTWFVVDFVS SIPVDYIFLI VEKGIDSEVY KTARALRIVR
301 FTKILSLLRL LRLSRLIRYI HQWEEIFHMT YDLASAVMRI CNLISMMLLL CHWDGCLQFL
361 VPMLQDFPSD CWVSINNMVN HSWSELYSFA LFKAMSHMLC IGYGRQAPES MTDIWLTMLS
421 MIVGATCYAM FIGHATALIQ SLDSSRRQYQ EKYKQVEQYM SFHKLPADFR QKIHDYYEHR
481 YQGKMFDEDS ILGELNGPLR EEIVNFNCRK LVASMPLFAN ADPNFVTAML TKLKFEVFQP
541 GDYIIREGTI GKKMYFIQHG VVSVLTKGNK EMKLSDGSYF GEICLLTRGR RTASVRADTY
601 CRLYSLSVDN FNEVLEEYPM MRRAFETVAI DRLDRIGKKN SILLHKVQHD LSSGVFNNQE
661 NAIIQEIVKY DREMVQQAEL GQRVGLFPPP PPPQVTSAIA TLQQAVAMSF CPQVARPLVG
721 PLALGSPRLV RRAPPGPLPP AASPGPPAAS PPAAPSSPRA PRTSPYGVPG SPATRVGPAL
781 PARRLSRASR PLSASQPSLP HGVPAPSPAA SARPASSSTP RLGPAPTART AAPSPDRRDS
841 ASPGAASGLD PLDSARSRLS SNL
```

TABLE 6

SEQ ID NO. 6 Nucleotide sequence of muHCN2

Accession number: MMJ225122

```
  1 CCGCTCCGCT CCGCACTGCC CGGCGCCGCC TCGCCATGGA TGCGCGCGGG GGCGGCGGGC
 61 GGCCGGGCGA TAGTCCGGGC ACGACCCCTG CGCCGGGGCC GCCGCCACCG CCGCCGCCGC
121 CCGCGCCCCC TCAGCCTCAG CCACCACCCG CGCCACCCCC GAACCCCACG ACCCCCTCGC
181 ACCCGGAGTC GGCGGACGAG CCCGGCCCGC GCGCCCGGCT CTGCAGCCGC GACAGCGCCT
```

TABLE 6-continued

SEQ ID NO. 6 Nucleotide sequence of muHCN2

Accession number: MMJ225122

```
 241   GCACCCCTGG CGCGGCCAAG GGCGGCGCGA ATGGCGAGTG CGGGCGCGGG GAGCCGCAGT
 301   GCAGCCCCGA GGGCCCCGCG CGCGGCCCCA AGGTTTCGTT CTCATGCCGC GGGGCGGCCT
 361   CCGGGCCCTC GGCGGCCGAG GAGGCGGGCA GCGAGGAGGC GGGCCCGGCC GGTGAGCCGC
 421   GCGGCAGCCA GGCTAGCTTC CTGCAGCGCC AATTCGGGGC GCTTCTGCAG CCCGGCGTCA
 481   ACAAGTTCTC CCTGCGGATC TTCGGCAGCC AGAAGGCCGT GGAGCGCGAG CAGGAACGCG
 541   TGAAGTCGGC GGGGGCCTGG ATCATCCACC CCTACAGCGA CTTCAGGTTC TACTGGGACT
 601   TCACCATGCT GTTGTTCATG GTGGGAAATC TCATTATCAT TCCCGTGGGC ATCACTTTCT
 661   TCAAGGACGA GACCACCGCG CCCTGGATCG TCTTCAACGT GGTCTCGGAC ACTTTCTTCC
 721   TCATGGACTT GGTGTTGAAC TTCCGCACCG GCATTGTTAT TGAGGACAAC ACGGAGATCA
 781   TCCTGGACCC CGAGAAGATA AAGAAGAAGT ACTTGCGTAC GTGGTTCGTG TGGACTTCG
 841   TGTCATCCAT CCCGGTGGAC TACATCTTCC TCATAGTGGA AAGGGAATC GACTCCGAGG
 901   TCTACAAGAC AGCGCGTGCT CTGCGCATCG TGCGCTTCAC CAAGATCCTC AGTCTGCTGC
 961   GGCTGCTGCG GCTATCACGG CTCATCCGAT ATATCCACCA GTGGGAAGAG ATTTTCCACA
1021   TGACCTACGA CCTGGCAAGT GCAGTGATGC GCATCTGTAA CCTGATCAGC ATGATGCTAC
1081   TGCTCTGCCA CTGGGACGGT TGCCTGCAGT TCCTGGTGCC CATGCTGCAA GACTTCCCCA
1141   GCGACTGCTG GGTGTCCATC AACAACATGG TGAACCACTC GTGGAGCGAG CTCTACTCGT
1201   TCGCGCTCTT CAAGGCCATG AGCCACATGC TGTGCATCGG CTACGGGCGG CAGGCGCCCG
1261   AGAGCATGAC AGACATCTGG CTGACCATGC TCAGCATGAT CGTAGGCGCC ACCTGCTATG
1321   CCATGTTCAT TGGGCACGCC ACTGCGCTCA TCCAGTCCCT GGATTCGTCA CGGCGCCAAT
1381   ACCAGGAGAA GTACAAGCAA GTAGAGCAAT ACATGTCCTT CCACAAACTG CCCGCTGACT
1441   TCCGCCAGAA GATCCACGAT TACTATGAAC ACCGGTACCA AGGGAAGATG TTTGATGAGG
1501   ACAGCATCCT TGGGGAACTC AACGGGCCAC TGCGTGAGGA GATTGTGAAC TTCAACTGCC
1561   GGAAGCTGGT GGCTTCCATG CCGCTGTTTG CCAATGCAGA CCCCAACTTC GTCACAGCCA
1621   TGCTGACAAA GCTCAAATTT GAGGTCTTCC AGCCTGGAGA TTACATCATC CGAGAGGGGA
1681   CCATCGGGAA GAAGATGTAC TTCATCCAGC ATGGGGTGGT GAGCGTGCTC ACCAAGGGCA
1741   ACAAGGAGAT GAAGCTGTCG GATGGCTCCT ATTTCGGGGA GATCTGCTTG CTCACGAGGG
1801   GCCGGCGTAC GGCCAGCGTG CGAGCTGACA CCTACTGTCG CCTCTACTCA CTGAGTGTGG
1861   ACAATTTCAA CGAGGTGCTG GAGGAATACC CCATGATGCG GCGTGCCTTT GAGACTGTGG
1921   CTATTGACCG GCTAGATCGC ATAGGCAAGA AGAACTCCAT CTTGCTGCAC AAGGTTCAGC
1981   ATGATCTCAG CTCAGGTGTG TTCAACAACC AGGAGAATGC CATCATCCAG GAGATTGTCA
2041   AATATGACCG TGAGATGGTG CAGCAGGCAG AGCTTGGCCA GCGTGTGGGG CTCTTCCCAC
2101   CACCGCCACC ACCGCAGGTC ACATCGGCCA TTGCCACCCT ACAGCAGGCT GTGGCCATGA
2161   GCTTCTGCCC GCAGGTGGCC CGCCCGCTCG TGGGGCCCCT GGCGCTAGGC TCCCCACGCC
2221   TAGTGCGCCG CGCGCCCCCA GGGCCTCTGC CTCCTGCAGC CTCGCCAGGG CCACCCGCAG
2281   CAAGCCCCCC GGCTGCACCC TCGAGCCCTC GGGCACCGCG GACCTCACCC TACGGTGTGC
2341   CTGGCTCTCC GGCAACGCGC GTGGGGCCCG CATTGCCCGC ACGTCGCCTG AGCCGCGCCT
2401   CGCGCCCACT GTCCGCCTCG CAGCCCTCGC TGCCCCATGG CGTGCCCGCG CCCAGCCCCG
2461   CGGCCTCTGC GCGCCCGGCC AGCAGCTCCA CGCCGCGCCT GGGACCCGCA CCCACCGCCC
```

TABLE 6-continued

SEQ ID NO. 6 Nucleotide sequence of muHCN2

Accession number: MMJ225122

```
2521  GGACCGCCGC GCCCAGTCCG GACCGCAGGG ACTCAGCCTC GCCGGGCGCT GCCAGTGGCC

2581  TCGACCCACT GGACTCTGCG CGCTCGCGCC TCTCTTCCAA CTTGTGACCC TTGAGCGCCG

2641  CCCCGCGGGC CGGGCGGGGC CGTCATCCAC ACCAAAGCCA TGCCTCGCGC CGCCCGCCCG

2701  TGCCCGTGCA GAAGCCATAG AGGGACGTAG GTAGCTTAGG AGGCGGGCGG CCCTGCGCCC

2761  GGCTGTCCCC CCATCGCCCT GCGCCCACCC CCATCGCCCC TGCCCCAGCG GCGGCCGCAC

2821  GGGAGAGGGA GGGGTGCGAT CACCTCGGTG CCTCAGCCCC AACCTGGGAC AGGGACAGGG

2881  CGGCCCTGGC CGAGGACCTG GCTGTGCCCC GCATGTGCGG TGGCCTCCGA GGAAGAATAT

2941  GGATCAAGTG CAATACACGG CCAAGCCGGC GTGGGGGTGA GGCTGGGTCC CCGGCCGTCG

3001  CCATGAATGT ACTGACGAGC CGAGGCAGCA GTGGCCCCCA CGCCCCATTA ACCCACAACC

3061  CCATTCCGCG CAATAAACGA CAGCATTGGC AAAAAAAAAA AA
//
```

TABLE 7

Abbreviations

| | |
|---|---|
| AKT | Arabidopsis thaliana K+ transport |
| cAMP | cyclic adenosine monophosphate |
| CHO | Chinese hamster ovary |
| EDTA | ethylenediamine tetraacetic acid |
| FLIPR | fluorescence imaging plate reader |
| HAC | hyperpolarization-activated cation channel; this name was used by some groups |

TABLE 7-continued

Abbreviations

| | |
|---|---|
| HCN | hyperpolarization-activated cyclic nucleotide gated cation channel; this is the new, generally accepted term |
| HEK | human embryonic kidney; |
| HEPES | N-2-hydroxyethylpiperazine-N'-2-ethanesulfonic acid |
| HTS | high-thoughput screening |
| KAT | K+ channel from Arabidopsis thaliana |

What is claimed is:

1. A process comprising
   a) providing, in a suitable container, cells that express a hyperpolarization-activated cation channel;
   b) hyperpolarizing the cells in the presence of a potential-sensitive fluorescent dye and an isoosmolar sodium-ion-free buffer;
   c) optionally, determining the membrane potential of the cells;
   d) simultaneously adding sodium ions and a sample containing at least one substance to be tested for its ability to modulate the activity of the cation channel;
   e) determining the membrane potential of the cells;
   f) determining whether the membrane potential changed upon simultaneous addition of sodium ions and the substance(s); and
   g) optionally, recording the change in membrane potential, wherein a change in membrane potential indicates the presence of at least one substance in the sample that modulates the activity of the cation channel.

2. The process of claim 1, wherein step c) is performed.

3. The process as claimed in claim 1, wherein the isoosmolar sodium-ion-free buffer comprises a potassium salt.

4. The process as claimed in claim 1, wherein the isoosmolar sodium-ion-free buffer comprises potassium ions at a concentration of at least 0.8 mM.

5. The process as claimed in claim 1, wherein the isoosmolar sodium-ion-free buffer comprises potassium ions at a concentration of at least 5 mM.

6. The process as claimed in claim 1, wherein the isoosmolar sodium-ion-free buffer comprises choline chloride or NMDG (N-methyl-D-glucamine).

7. The process as claimed in claim 1, wherein the potential-sensitive dye is an oxonol derivative.

8. The process as claimed in claim 7, wherein the oxonol derivative is a 3-bis-barbituric acid oxonol.

9. The process as claimed in claim 8, wherein the 3-bis-barbituric acid oxonol is bis-(1,3-dibutylbarbituric acid) trimethine oxonol [$DiBac_4(3)$], bis-(1,3-diethylthiobarbituric acid)trimethine oxonol, bis-(1,3-dibutylbarbituric acid)pentamethine oxonol, or a combination of these.

10. The process as claimed in claim 1, wherein the potential-sensitive fluorescent dye used is suitable for use in fluorescent imaging plate reader system.

11. The process as claimed in claim 1, wherein cells having an elevated intracellular cAMP concentration are used.

12. The process as claimed in claim 11, wherein the intracellular cAMP concentration is increased by addition of dibutyryl-cAMP or 8-bromo-cAMP.

13. The process as claimed in claim 11, wherein the intracellular cAMP concentration is increased by addition of an adenylate cyclase activator.

14. The process as claimed in claim 11, wherein the intracellular cAMP concentration is increased by addition of forskolin.

15. The process as claimed in claim 14, wherein the intracellular cAMP concentration is increased by addition of from 1 pM to 100 pM of forskolin.

16. The process as claimed in claim 11, wherein the intracellular cAMP concentration is increased by addition of receptor ligands.

17. The process as claimed in claim 1, wherein the hyperpolarization-activated cation channel is HCN1, HCN2, HCN3, HCN4, KAT1, or a heteromultimer of these channels.

18. The process as claimed in claim 1, wherein the hyperpolarization-activated cation channel is a human hyperpolarization-activated cation channel.

19. The process as claimed in claim 1, wherein the cells are mammalian cells.

20. The process as claimed in claim 19, wherein the cells are CHO or HEK cells.

21. The process as claimed in claim 1, wherein the cells contain a plasmid which comprises the cDNA of a hyperpolarization-activated cation channel.

22. The process as claimed in claim 1, wherein the cells comprise a second plasmid, which comprises the cDNA of the same hyperpolarization-activated cation channel.

23. The process as claimed in claim 22, wherein the cells comprise a second plasmid, which comprises the cDNA of a different hyperpolarization-activated cation channel, such that heteromultimeric HCN channels can be formed.

24. The process as claimed in claim 1, wherein the cells comprise a plasmid, which comprises synthetic cDNA encoding at least part of at least two different cation channels.

25. The process as claimed in claim 1, wherein a change in membrane potential is measured using a potential-sensitive fluorescent dye.

26. The process as claimed in claim 25, wherein the potential-sensitive fluorescent dye is an oxonol derivative.

27. The process as claimed in claim 26, wherein the oxonol derivative is 3-bis-barbituric acid oxonol.

28. The process as claimed in claim 1, wherein at least one measurement is carried out in a Fluorescent Imaging Plate Reader (FLIPR).

29. The process as claimed in claim 1, wherein the change of the membrane potential of at least two cells is compared.

30. The process as claimed in claim 1, wherein the process is a high-throughput screening process.

31. The process as claimed in claim 1, wherein the hyperpolarization-activated cation channel is HCN1, HCN2, HCN3, HCN4, KAT1, or a heteromultimer of these channels.

* * * * *